US005962410A

United States Patent [19]

Jaynes et al.

[11] Patent Number: 5,962,410
[45] Date of Patent: Oct. 5, 1999

[54] INHIBITION OF EUCARYOTIC PATHOGENS WITH LYTIC PEPTIDES

[75] Inventors: Jesse M. Jaynes; Frederic M. Enright; Kenneth L. White, all of Baton Rouge, La.

[73] Assignee: Helix Biomedix, Inc., Baton Rouge, La.

[21] Appl. No.: 08/301,733

[22] Filed: Sep. 6, 1994

Related U.S. Application Data

[63] Continuation of application No. 07/976,680, Nov. 16, 1992, abandoned, which is a continuation of application No. 07/841,852, Feb. 26, 1992, abandoned, which is a continuation of application No. 07/102,175, Sep. 29, 1987, abandoned, which is a continuation-in-part of application No. 07/069,653, Jul. 7, 1987, abandoned.

[51] Int. Cl.⁶ ............................ A61K 38/10; A61K 38/16
[52] U.S. Cl. .............................. 514/12; 514/13; 530/324; 530/326
[58] Field of Search ............................ 435/259; 530/326, 530/324, 310; 514/2, 8, 12, 13

[56] References Cited

U.S. PATENT DOCUMENTS

| | | | |
|---|---|---|---|
| 4,355,104 | 10/1982 | Hultmark et al. | 435/70 |
| 4,520,016 | 5/1985 | Hultmark et al. | 514/12 |
| 4,579,821 | 4/1986 | Palmiter et al. | 435/91.41 |
| 4,643,988 | 2/1987 | Segrest et al. | 514/12 |
| 4,704,362 | 11/1987 | Itakura et al. | 435/252.3 |
| 5,045,531 | 9/1991 | Berkowitz | 514/12 |
| 5,206,154 | 4/1993 | Lai | 435/69.7 |
| 5,208,220 | 5/1993 | Berkowitz | 514/13 |
| 5,773,413 | 6/1998 | Jaynes et al. | 514/12 |

FOREIGN PATENT DOCUMENTS

| | | |
|---|---|---|
| 0157351 | 10/1985 | Germany . |
| 0182278 | 5/1986 | Germany . |
| 063949 | 11/1982 | United Kingdom . |
| 145338 | 6/1985 | United Kingdom . |
| 0184288 | 6/1986 | United Kingdom . |
| WO86/04356 | 7/1986 | WIPO . |
| WO89/00199 | 1/1989 | WIPO . |

OTHER PUBLICATIONS

S. Barr et al., "Activity of Lytic Peptides against Intracellular *Trypanosoma cruzi* Amastigotes in vitro and Parasitemias in Mice," *Journal of Parasitology*, vol. 81, pp. 974–978 (1995).

A. Baghian et al., "An Amphipathic α–Helical Synthetic Peptide Analogue of Melittin Inhibits Herpes Simplex Virus–1 (HSV–1)–Induced Cell Fusion and Virus Spread," *Peptides*, vol. 18, pp. 177–183 (1997).

M. Arrowood et al., "Hemolytic Properties of Lytic Peptides Active against the Sporozoites of *Cryptosporidium parvum*," *Journal of Protozoology*, vol. 38, pp. 161S–163S (1991).

M. Arrowood et al., "In Vitro Activities of Lytic Peptides against the Sporozoites of *Cryptosporidium parvum*," *Antimicrobial Agents and Chemotherapy*, vol. 35, pp. 224–227 (1991).

Anderson, Lucy, *J. Cell Sci.*, "Protein Synthesis and Uptake by Isolated Cecropia Ooctyes", 1971, 8:735–750.

Andreu, D., *Proc. Natl. Acad. Sci.*, "Solid–phase synthesis of Cecropin A and Related Peptides", 1983, 80:6475–6479.

Andreu, D., *Biochemistry*, "N–Terminal Analogues of Cecropin A: Synthesis, Antibacterial Activity, and Conformation Properties", 1985, 24:1683–1688.

Bernheimer, A.W., *Biochimica et Biophysica Acta*, "Interactions between Membranes and Cytolytic Peptides", 1986, 86:123–141.

Bessler, W.G., *Biochemical and Biophysical Research Communications*, "Interaction of Membrane Modifying Peptide Antibiotics from *Trichoderma viride* with Leukocytes", 1979, 87:99–105.

Blasi, Udo, *Gen. Virol.*, "Influence of C–terminal Modifications of ΦX74 Lysis Gene E on its Lysis–inducing Properties", 1985, 66:1209–1213.

Boller, Thomas, *UCLA Symp. Mol. Cell. Biol.*, Newser, Induction of Hydrolases as a Defense Reaction Against Pathogens, 1985 (Cell. Mol. Biol. Plant Stress).

Boman, H.G., *Developmental and Comparative Immunology*, "On the Primary Structures of Lysozyme, Cecropins and Attacins from *Hyalophora cecropia*", 1985, 9:551–558.

Boman, H.G., *Ann. Rev. Microbiol.*, "Cell–Free Immunity in Insects", 1987 41:103–26.

Brillinger, G.U., *Arch. Microbiol*, "Metabolic Products of Microorganisms 181*. Chitin Synthase from Fungi, a Test Model for Substances with Insecticidal Properties", 1979, 121:71–74.

Buckley, K.J., *Mol. Gen. Genet*, "Lytic Activity Localized to Membrane–spanning Region of ΦX174 E Protein", 1986, 204:120–125.

Chen, Hao–Chia, *FEBS Letters*, "Synthetic Magainin Analogues with Improved Antimicrobial Activity", 1988, 236:462–466.

Christensen, Bernd, *Proc. Natl. Acad. Sci.*, "Channel–forming Properties of Cecropins and Related Model Compounds Incorporated into Planar Lipid Membranes", 1988, 85:5072–5076.

(List continued on next page.)

*Primary Examiner*—Brian R. Stanton
*Assistant Examiner*—Deborah J. R. Clark
*Attorney, Agent, or Firm*—Arnold White & Durkee

[57] ABSTRACT

Inhibition of eucaryotic pathogens and neoplasms and stimulation of lymphocytes and fibroblasts with lytic peptides such as cecropins and sarcotoxins. Eucaryotic cells are contacted with cecropin or sarcotoxin, or a synergistic combination of cecropins or sarcotoxin with lysozyme, in an amount effective to lyse or inhibit the cells. Target cells include eucaryotic microorganisms such as protozoa, e.g. *T. cruzi* and *P. falciparum*, mammalian lymphomas and leukemias, and cells infected with intracellular pathogens such as viruses, bacteria and protozoa. Also disclosed is a method for stimulating proliferation of lymphocytes and fibroblasts by contacting such cells with an effective amount of cecropin or sarcotoxin. The methods may be in vitro or in vivo.

32 Claims, 9 Drawing Sheets

OTHER PUBLICATIONS

Cuervo, Julio H., *Peptide Research*, "The Magainins: Sequence Factors Relevant to Increased Antimicrobial Activity and Decreased Hemolytic Activity", 1988, 1:81–86.

Deshpande, M.V., *Journal of Scientific and Industrial Research*, "Enzymatic Degradation of Chitin & Its Biological Applications", 1986, 45:273–281.

Drutz, David, *Basic & Clinical Immunology*, "Immunity & Infection", 1984, 197–201.

Eglitis, Martin A., *Science*, "Gene Expression in Mice After High Efficiency Retroviral–Mediated Gene Transfer", 1985, 230:1395–1398.

Engstrom, A., *The EMBO Journal*, "Insect Immunity. The Primary Structure of the Antibacterial Protein Attacin F and its Relation to Two Native Attacins from *Hyalophora cecropia*", 1984, 3:2065–2070.

Engstrom, A., *The EMBO Journal*, "Amino Acid and cDNA Sequences of Lysozyme from *Hyalophora cecropia*", 1985, 4:2119–2122.

Fingl, Edward, *The Pharmacological Basis of Therapeutics*, "General Principles" Chapter 1, 1975. pp. 1–2.

Fuchs, R.L., *Applied and Environmental Microbiology*, "Cloning of a *Serratia marcescens* Gene Encoding Chitinase", 1986, 51:504–509.

Garcia, Lopez, *Biochem Genetics*, "Production of Lysozyme of *Streptococcus pneumonia* in *Escherichia coli* by Recombinant DNA Technology", 1986 106:190368d.

Garrett, Jinnie, *Mol. Gen. Genet.*, "Cell Lysis by Induction of Cloned Lambda Lysis Genes", 1981, 182:326–331.

Gelehrter, Thomas D., *Biochem. and Biophys. Res. Comm.*, Stimulation of Monovalent Ion Fluxes and DNA Synthesis in 3T3 Cells by Melittin and Vasopressin is not Medeated by Phospholiped Deacylation, 1980, 97:716–724.

Goy, P., *Agro. Division Report*, "Spectrum of Activity of 1 Synthetic Cecropin: In Vitro and In Vivo Tests", 12 F Report 89013xx, Oct. 18, 1989.

Horwitz, Marc, *Mammalian Hormones*, "Genetic Improvement of Chitinase Production by *Serratia marcescens*", 1985, 102:216038R.

Hultmark, D., *Eur. J. Biochem.*, "Insect Immunity. Purification and Properties of Three Inducible Bactericidal Proteins from Hemolymph of Immunized Pupae of *Hyalophora cecropia*", 1980, 106:7–16.

Hultmark, D. *Eur. J. Biochem.*, "Insect Immunity: Isolation and Structure of Cecropin D Four Minor Antibacterial Components from Cecropia Pupae", 1982, 127:207–217.

Hultmark, D., *The EMBO Journal*, "Insect Immunity. Attacins, a Family of Antibacterial Proteins from *Hyalophora cecropia*", 1983, 2:571–576.

Huszar, D., *Proc. Natl. Acad. Sci. USA*, "Insertion of a Bacterial Gene the Mouse Germ Line Using an Infectious Retrovirus Vector", 1985, 82:8587–8591.

Jaynes, J.M., Departments of Biochemistry, Vet Science and Animal Science, L.S.U. "In Vitro Effect of Novel Lytic Peptides on *Plasmodium falciparum* and *Trypanosoma cruzi*" (date unknown).

Jaynes, J.M., *FASEB Journal*, "In Vitro Cytocidal Effect of Novel Lytic Peptides on *Plasmodium falciparum* and *Trypanosoma cruzi*", 1988, 2:2878–2883.

Jaynes, J.M., *Peptide Research*, "In Vitro Cytocidal Effect of Lytic Peptides on Several Transformed Mammalian Cell Lines", 1989.

Jaynes, J.M., *Drug News & Perspectives*, "Lytic Peptides Portend an Innovative Age in the Management and Treatment of Human Disease", 1990, 3:69–78.

Kockum, K., *The EMBO Journal*, "Insect Immunity. Isolation and Sequence of Two cDNA Clones Corresponding to Acidic and Basic Attacins from *Hyalophora cecropia*", 1984, 3:2071–2075.

Lee, J.Y., *The EMBO Journal*, "Insect Immunity. Isolation of cDNA Clones Corresponding to Attacins and Immune Protein P4 from *Hysalphora cecropia*" 1983, 2:577–581.

Merrifield, R.B., *Biochemistry*, "Synthesis of the Antibacterial Peptide Cecropin A(1–33)", 1982, 21:5020–5031.

Nakai, T., *Chemical Abstracts*, "Synthesis of Self–defense Substance Produced by Silkworm, Lepidopteran, and Related Peptides", 106:214351w, 1986.

Nakajima, Yuki, *Biological Chemistry*, "Interaction Between Liposomes and Sarcotoxin IA, a Potent Antibacterial Protein of *Sarcophga peregrina* (Flesh Fly)*", 1987, 262:1665–1669.

Natori, S., *Drugs of the Future*, "Future Drugs Mimicking Insect Defense proteins: Sarcophaga Lectic and Sarcotozin I", 1988, 13:59–68.

Okada, Masayuki, *Biochem. J.*, "Ionophre Activity of Sarcotoxin I, a Bactericidal Protein of *Sarcophaga peregrina*", 1985, 229:453–458.

Partial Search Report for European Patent Application EP 88 90 6595 Jun. 27, 1991.

Partial Search Report for European Application No. EP 90 90 6453 Jun. 19, 1992.

Patent Cooperation Treaty International Search Report for International Application No. PCT/US88/02272, Nov. 15, 1988.

Patent Cooperation Treaty International Search Report for International Application No. PCT/US90/01945, Jul. 30, 1990.

Shiba, T., *Chemical Abstracts*, "Antimicrobial Peptides from Silkworm Hemolymph", 104:230430k, 1985.

Skogen, William F., Blood, Fibrinogen–Derived Peptide BB1–42 is a Multidomained Neutrophil Chemoattractant, 1988, 71:1475–1479.

Steiner, H., *Nature*, "Sequence and Specificity of two Antibacterial Proteins Involved in Insect Immunity", 1981, 292:246–248.

Supplementary Search Report for European Patent Application No. EP 88 90 6511, Jan. 18, 1991.

Van Hofsten, P. *Proc. Natl. Acad. Sci. USA*, "Molecular Cloning, cDNA Sequencing, and Chemical Synthesis of Cecropin B from *Hyalophora cecropia*", 1985, 82:2240–2243.

INHIBITION OF EUCARYOTIC PATHOGENS WITH LYTIC PEPTIDES

CROSS REFERENCE TO RELATED APPLICATIONS

This is a continuation of U.S. Ser. No. 07/976,680, filed Nov. 16, 1992, now abandoned; which is a continuation of U.S. Ser. No. 07/841,852, filed Feb. 26, 1992, now abandoned, which is a continuation of U.S. Ser. No. 07/102,175, filed Sep. 29, 1987, now abandoned; which is a continuation-in-part of U.S. Ser. No. 07/069,653, filed Jul. 7, 1987 by Jesse M. Jaynes, Frederick M. Enright and Kenneth L. White, which is now abandoned, and which is hereby incorporated herein by reference. U.S. Ser. No. 889,225, filed Jul. 25, 1986 by Jaynes and Kenneth S. Derrick which relates to the genetic transformation of plants with genes expressing lytic peptides to provide such plants with resistance to pathogens and pests is also related to the present invention and is hereby incorporated herein by reference.

FIELD OF THE INVENTION

The present invention relates to lytic peptides, their use in methods for inhibiting eucaryotic pathogens, cancer cells and intracellularly infected cells, and their use in methods for stimulating the proliferation of fibroblasts and lymphocytes. More particularly, this invention relates to the inhibition of such pathogens, cancers and infected cells, and the stimulation of fibroblasts and lymphocytes in mammals and other higher animals.

BACKGROUND OF THE INVENTION

Many diseases of procaroytic origin, i.e. caused by pathogenic bacteria, are known. Such diseases are in general more easily treated than those of eucaryotic origin because of the marked differences between the invading procaryotes and the eucaryotic cells of the host. Thus, because of the differences between bacterial cells and those of the host, many antibiotics are known to specifically inhibit the invading bacteria without significant adverse effects on the host. In contrast, it has generally been more difficult to treat diseases of nonbacterial origin, such as malaria, sleeping sickness and Chagas disease.

The property of certain peptides to induce lysis of procaryotic microorganisms such as bacteria are known. For example, U.S. Pat. Nos. 4,355,104 and 4,520,016 to Hultmark et al describe the bacteriolytic properties of some cecropins against Gram-negative bacteria. Quite interestingly, the cecropins described in the Hultmark et al patents were not universally effective against all Gram-negative bacteria. For example, the cecropins described therein lysed *Serratia marcescens* D61108, but not *Serratia marcescens* D611. Moreover, cecropins have heretofore been reported to have no lytic activity towards eucaryotic cells such as insect cells, liver cells and sheep erythrocytes, as reported in the Hultmark patents; International Patent Publication WO/8604356; Andreu et al, *Biochemistry*, vol. 24, pp. 1683–88 (1985); Boman et al, *Developmental and Comparative Immunology*, vol. 9, pp. 551–558 (1985); and Steiner et al, *Nature*, vol. 292, pp. 246–248 (1981).

Other lytic peptides heretofore known include, for example, the sarcotoxins and lepidopterans. Such peptides generally occur naturally in the immune system of *Sarcophaga peregrina* and the silkworm, lepidopteran, respectively, as reported in Nakajima et al, *The Journal of Biological Chemistry*, vol. 262, pp. 1665–1669 (1987) and Nakai et al, *Chem. Abst.* 106:214351w (1987).

The mechanism of action of the lytic peptides in the immune systems in which they occur is not entirely clear. There must, of course, be some aspect of the mechanism which regulates the specificity of the lytic peptides for invading pathogens among the cells of the host organism which must generally be preserved from lysis. For example, human complement fixation involves antibodies which are generally specific for certain antigens expressed by the invading pathogen. The activated components of complement attack the membrane of the invading cell to which they are bound by the antigen-antibody reaction to produce circular lesions which are probably formed as a result of insertion of the C9 protein into the membrane. The more primitive mechanisms involved in insect immunology are less specific, but the peptides involved apparently do not significantly lyse the host cells.

There are many differences between the membranes of different types of cells which can affect their susceptibility to lysis by the various lytic peptides. As suggested above, for example, some proteins are capable of lysing only cells expressing an appropriate antigen for the antibody associated with such protein. Thus, it is not surprising that the less specific lytic peptides such as cecropins are more capable of lysing procaryotes than the eucaryotic cells of the insect.

Gram-positive procaryotes generally have a thicker cell wall than Gram-negative ones. Also, Gram-positive cell membranes have a cytoplasmic membrane and a cell wall containing mostly peptidoglycans and teichoic acids, whereas Gram-negative cell membranes have an inner cell wall consisting entirely of peptidoglycan and associated proteins surrounded by an outer cell wall comprised of lipid, lipopolysaccharide and protein. In contrast, eucaryotic cells generally have a plasma membrane comprising a lipid bilayer with proteins and carbohydrates interspersed therein, and also have organelles with their own membrane systems, but generally do not have an outer cell wall. It is readily appreciated that the considerable variation of membrane structures among bacteria (procaryotes) accounts for considerable variation in their susceptibility to lysis by the various insect immune proteins.

The variation of membrane structures among eucaryotes is also considerable, but these membranes generally comprise phospholipid molecules in a bilayer arrangement with a thickness of about 50 Å. The hydrophilic portion of the phospholipid is generally oriented to the exterior and interior surfaces of the membrane, while the hydrophobic portions are generally found in the interior region of the membrane between the hydrophilic surfaces. As reported in Nakajima et al, the presence of cholesterol and the assymetric distribution of phospholipids in the cytoplasmic membrane of eucaryotic cells may explain the selective toxicity of sarcotoxin to bacteria. Since cholesterol causes condensation of the phospholipid bilayers, it can hinder the penetration of lytic peptides into the cytoplasmic membrane of eucaryotic cells. Similarly, the predominance of neutral phospholipids in the outer monolayer of eucaryotic membranes would result in less affinity to positively charged lytic peptides such as cecropin and sarcotoxin than acidic phospholipids generally located on the cytoplasmic side of the membrane.

A number of the antibacterial polypeptides have been found to be useful when the genes encoding therefor are incorporated into various plant species. Particularly, when introduced into the plant genome by means of an Agrobacterium plasmid vector, the antibacterial polypeptide-encoding genes produce plant species much more resistant to certain bacterially induced disease conditions and plant pathogens. Such antibacterial polypeptides and the transformation of plants with genes encoding therefor are described in aforementioned U.S. patent application Ser. No. 889,225.

Polynucleotide molecules expressible in a given host and having the sequence araB promoter operably linked to a gene which is heterologous to such host are also known. The heterologous gene codes for a biologically active polypeptide. A genetic construct of a first genetic sequence coding for cecropin operably linked to a second genetic sequence coding for a polypeptide which is capable of suppressing the biological effect of the resulting fusion protein towards an otherwise cecropin-sensitive bacterium is also described in International Publication W086/04356, Jul. 31, 1986.

The Hultmark et al patents mentioned above also mention that there are no known antibodies to cecropin, indicating a wide acceptability for human and veterinary applications, including one apparently useful application for surface infections because of the high activity against pseudomonas. Similarly, EPO publication 182,278 (1986) mentions that sarcotoxins may be expected to be effective in pharmaceutical preparations and as foodstuff additives, and that antibacterial activity of sarcotoxin can be recognized in the presence of serum. Shiba, *Chem. Abstr.* 104: 230430K (1985) also mentions preparation of an injection containing 500 mg lepidopteran, 250 mg glucose and injection water to 5 ml.

Several analogs of naturally-occurring cecropins, sarcotoxins and lepidopterans have been reported. For example, it is reported in Andreu et al, *Proc. Natl. Acad. Sci. U.S.A.*, vol. 80, pp. 6475–6479 (1983) that changes in either end of the amino acid sequence of cecropin generally result in losses in bactericidal activity in varying degrees against different bacteria. It is reported in Andreu et al (1985) mentioned above that $Trp^2$ is clearly important for bactericidal activity of cecropin, and that other changes in the 4, 6 or 8 position have different effects on different bacteria. From the data given in Table II at page 1687 of Andreu et al (1985), it appears that almost any change from natural cecropin generally adversely affects its bactericidal activity. Cecropin is defined in International Publication W086/04356 to include bactericidally active polypeptides from any insect species and analogs, homologs, mutants, isomers and derivatives thereof having bactericidal activity from 1% of the naturally-occurring polypeptides up to 100 times or higher activity of the naturally-occurring cecropin. Other references generally discuss the effects of the α-helix conformation and the amphiphilic nature of cecropin and other lytic peptides.

It is known that lysozyme and attacins also occur in insect hemolymph. For example, it is reported in Okada et al, *Biochem. J.*, vol. 229, pp. 453–458 (1985) that lysozyme participates with sarcotoxin against bacteria, but that the bactericidal actions are diverse. Steiner et al mentioned above suggests that lysozyme plays no role in the antibacterial activity of insect hemolymph other than to remove debris following lysis of bacteria by cecropin. Merrifield et al, *Biochemistry,* vol. 21, pp. 5020–5031 (1982) and Andreu et al (1983) mentioned above state that cecropin purified from insect hemolymph may be contaminated with lysozyme, but demonstrate that the synthetically prepared cecropin is as bactericidally active as purified cecropin from insect hemolymph.

SUMMARY OF THE INVENTION

It has now been found that lytic peptides are effective against certain eucaryotic cells which are a source of disease in higher animals. Lytic peptides are capable of lysing protozoa, fungi, cancer cells and eucaryotic cells infected with an intracellular pathogen; and, yet, by appropriate selection of the lytic peptide, will not generally lyse the normal cells of the host animal. Thus, lytic peptides can be used in vitro to lyse the membranes of certain eucaryotic cells. More importantly, the lytic peptides can be used in vivo to treat or prevent cancer and pathogenic diseases of eucaryotic origin in higher animals. This discovery is quite surprising and unexpected in view of the apparently unanimous conclusions of prior researchers that lytic peptides do not lyse eucaroytic cells.

Also quite surprisingly, it has been found that certain lytic peptides such as, for example, the cecropins, are effective to stimulate the proliferation of mammalian fibroblasts and lymphocytes. Thus, the cecropins are useful in enhancing the production of products obtained from the in vitro culturing of such cells. More importantly, the cecropins can be used in vivo in the treatment of mammals to accelerate the regenerative processes associated with disease and injury by stimulating lymphocytes and fibroblasts in the injured mammal.

Accordingly, the invention provides a method for lysing eucaryotic cells which includes contacting the cells with a lytic peptide in an amount effective to lyse the cells. The cells are eucaryotic microorganisms, lymphomas, leukemias or carcinomas, or eucaryotic cells infected with an intracellular pathogenic microorganism. The lytic peptide has from about 30 to about 40 amino acids, at least a portion of which are arranged in an amphiphilic α-helical conformation. The peptide has a substantially hydrophilic head with a positive charge density and a substantially hydrophobic tail. The conformation has a predominantly hydrophobic face along the length of the conformation and a predominantly hydrophilic face opposed therefrom.

The invention also provides a method for selectively lysing eucaryotic cells in the presence of cells which are not lysed. The method includes contacting target eucaryotic cells in the presence of non-target cells with a selectively lytic, free peptide in an amount effective to lyse the target cells. The target cells are eucaryotic microorganisms, lymphomas, leukemias or carcinomas, or eucaryotic cells infected with an intracellular pathogenic microorganism. The lytic peptide contains from about 30 to about 40 amino acids, at least a portion of which are arranged in an amphiphilic α-helical conformation.

In another aspect, the invention provides a method for lysing eucaryotic microorganisms which includes contacting the eucaryotes with an amount of a lytic peptide effective to lyse the microorganisms. The peptide includes from about 30 to about 40 amino acids, at least a portion of which are arranged in an amphiphilic α-helical conformation.

In still another aspect, the invention provides a method for lysing cancer cells. The method includes contacting lymphoma, leukemia or carcinoma cells with an effective amount of a lytic peptide to lyse the cells. The peptide has from about 30 to about 40 amino acids at least a portion of which are arranged in an amphiphilic α-helical conformation.

Further, the invention provides a method for selectively lysing infected eucaryotic cells. The infected eucaryotic cells are infected with an intracellular pathogenic microorganism, such as, for example, virus, bacteria, fungi or protozoa. The method includes contacting the infected and uninfected cells with a selectively lytic, free peptide in an amount effective to selectively lyse the infected cells and leave the uninfected cells substantially free of lysis.

Still further, the invention provides a method for inhibiting eucaryotic cells in a higher animal. The method includes introducing a selectively lytic, free peptide into the higher animal in an amount effective to inhibit therein eucaryotic cells such as eucaryotic microorganisms, mammalian lymphomas, leukemias or carcinomas, or cells infected with an intracellular pathogenic microorganism.

Still further, the invention provides a method for stimulating the proliferation of normal mammalian fibroblasts and lymphocytes which includes contacting the fibroblasts or lymphocytes with a stimulating peptide in an amount effective to stimulate the proliferation thereof. There is also provided a method for stimulating the proliferation of normal fibroblasts and lymphocytes in a mammal which includes introducing a stimulating peptide into a mammal in an amount effective to stimulate the proliferation of fibroblasts or lymphocytes therein.

In other aspects, the invention provides a synergistic bactericidal composition containing lytic peptide and lysozyme, and novel lytic peptides.

DESCRIPTION OF THE INVENTION

Figure 1:
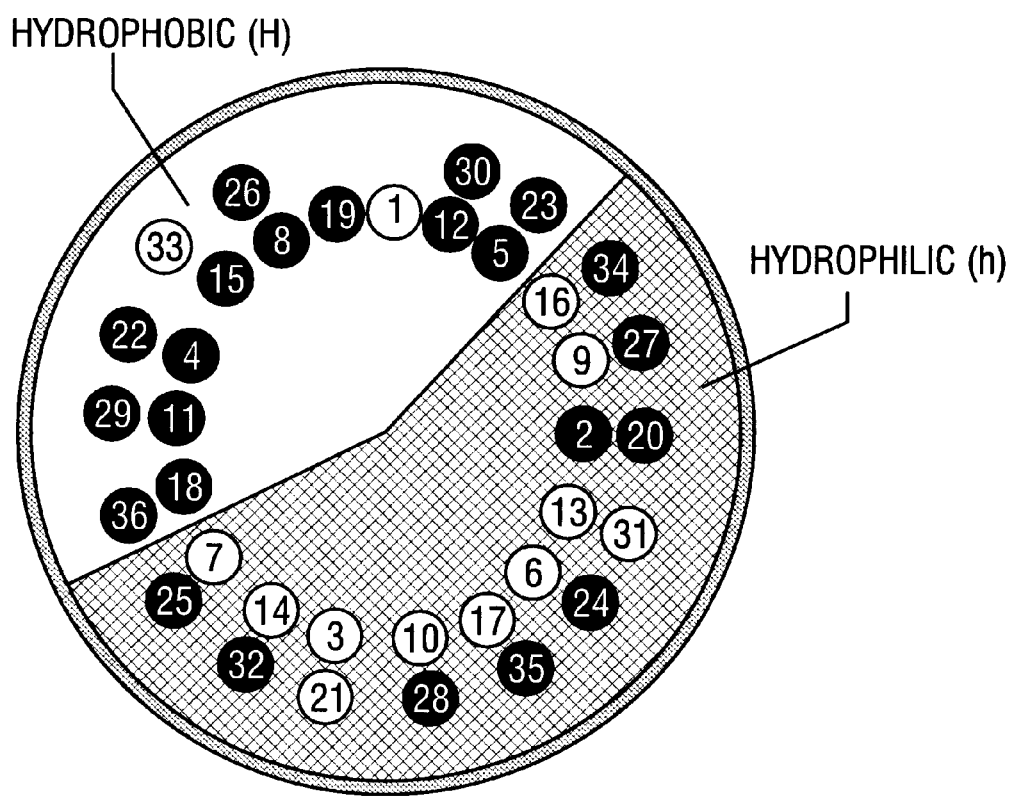
FIG. 1 is an Edmundson helical wheel construct for cecropin B.
Figure 2:
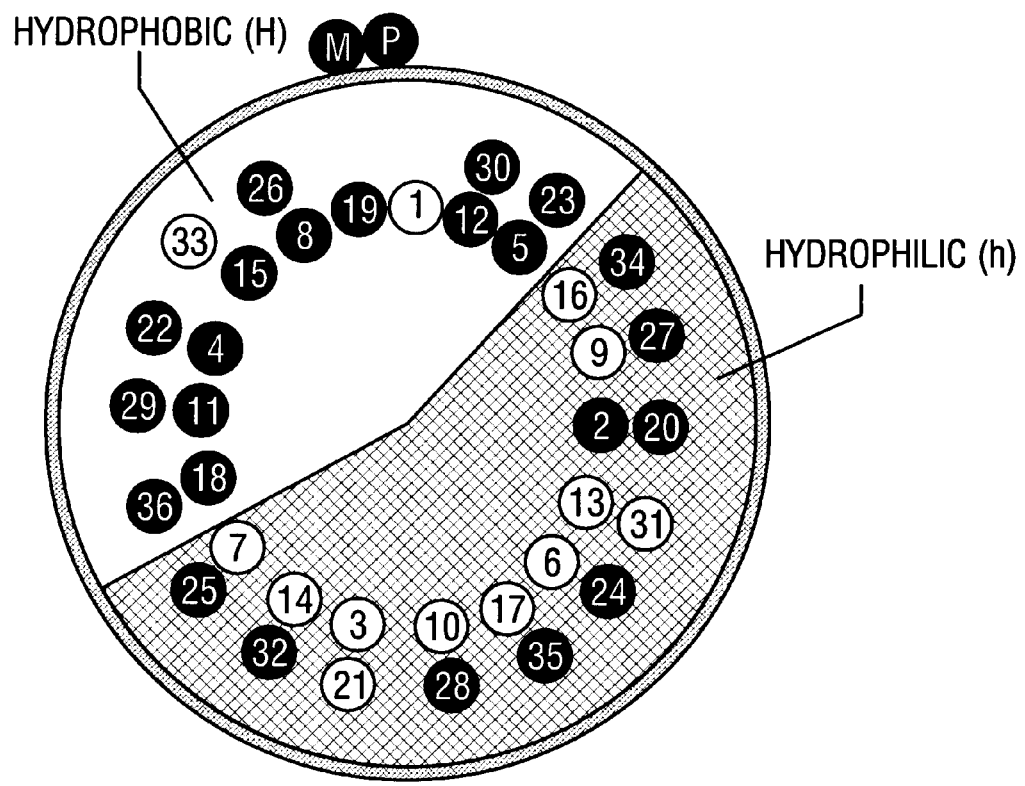
FIG. 2 is an Edmundson helical wheel construct for cecropin SB-37.
Figure 3:
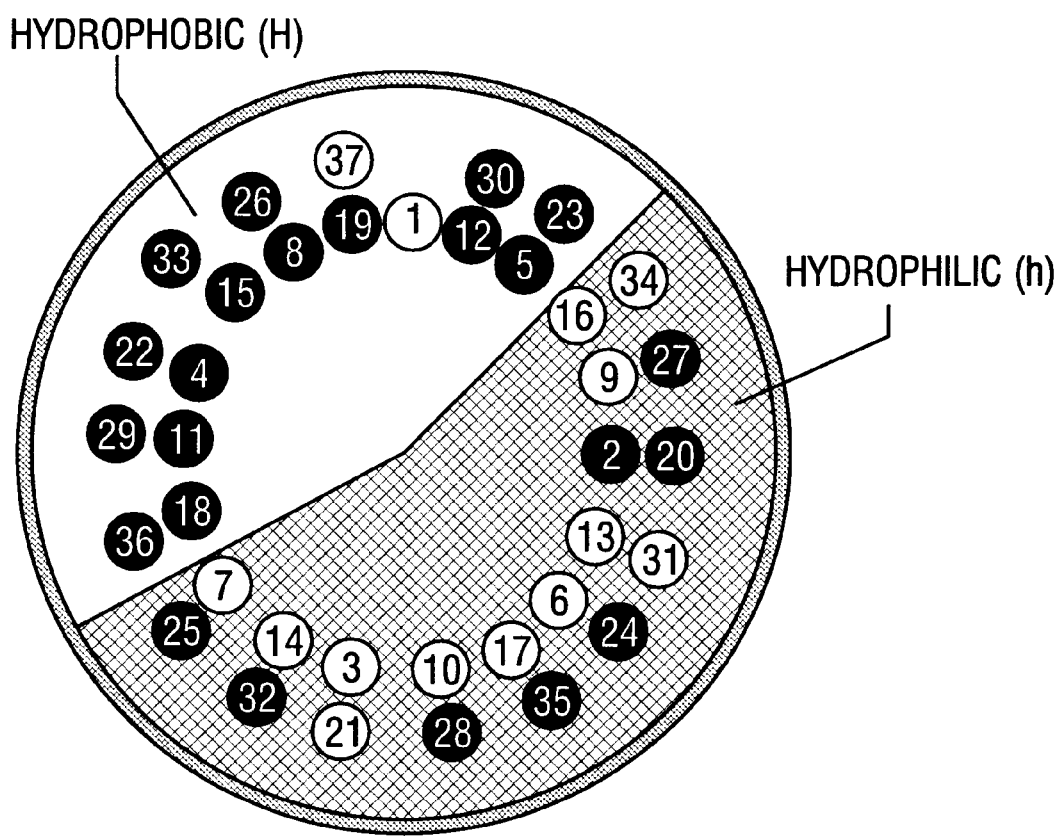
FIG. 3 is an Edmundson helical wheel construct for cecropin A.
Figure 4:
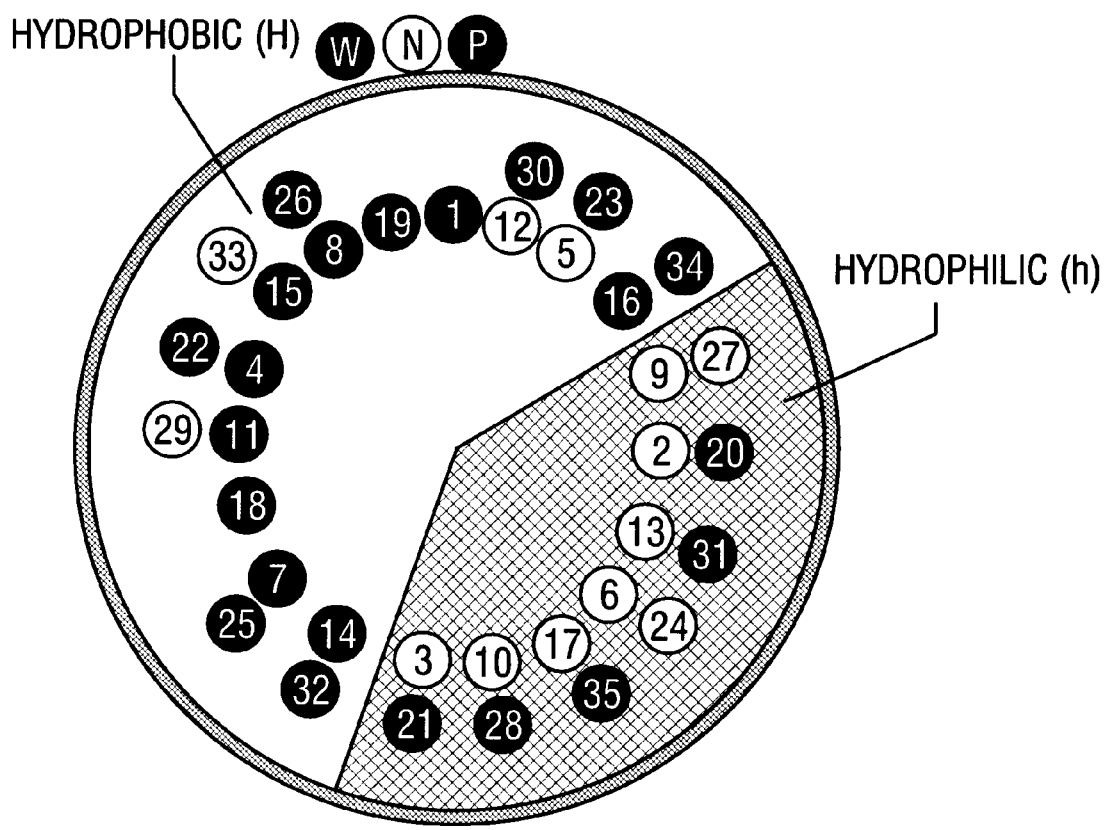
FIG. 4 is an Edmundson helical wheel construct for cecropin D.

It has been found that lytic peptides having about 30–40 amino acids are capable of lysing or otherwise inhibiting eucaryotic cells which are used for the production of biological products and/or are involved in the disease or illness of higher animals. Such eucaryotic cells include, for example, protozoa, fungi, algae, cancer cells such as lymphomas, leukemias and carcinomas, and cells infected with intracellular fungi, bacteria, protozoa or viruses. On the other hand, certain lytic peptides have also been found to stimulate the proliferation of lymphocytes and fibroblasts.

As used herein, the term "lytic peptide" includes any polypeptide which lyses the membrane of a cell in an in vivo or in vitro system in which such activity can be measured. Suitable lytic peptides used in the present invention have lytic activity toward one or more eucaryotic cells such as protozoa, fungi, helminths, leukemias, lymphomas or carcinomas, or cells infected by intracellular pathogens. Preferred lytic peptides have from about 30 to about 40 amino acids, at least a portion of which are arranged in an amphiphilic α-helical conformation having a substantially hydrophilic head with a positive charge density, a substantially hydrophobic tail, and a pair of opposed faces along the length of the helical conformation, one such face being predominantly hydrophilic and the other being predominantly hydrophobic. The head of this conformation may be taken as either the amine terminus end or the carboxy terminus end, but is preferably the amine terminus end.

A "selectively lytic peptide" is a lytic peptide which preferentially lyses target cells in a system comprising both target and non-target cells, wherein the target cells are selected from protozoa, fungi, mammalian leukemias, lymphomas and carcinomas and eucaryotic cells infected by intracellular pathogens. The selectively lytic peptides used in the present methods are preferably "free peptides," i.e. undirected in action by an antibody and otherwise unbound or unfused to another molecular fragment which adversely affects its lytic activity.

Suitable lytic peptides generally include cecropins such as cecropin A, cecropin B, cecropin D, and lepidopteran; sarcotoxins such as sarcotoxin IA, sarcotoxin IB, and sarcotoxin IC; and other polypeptides obtainable from the hemolymph of any insect species which have lytic activity against bacteria similar to that of the cecropins and sarcotoxins. It is also contemplated that lytic peptides may be obtained as the lytically active portion of larger peptides such as attacins; lysozymes; certain phage proteins such as S protein of λ phage, E protein of PHIX 174 phage and P13 protein of P22 phage; and C9 protein of human complement. As used herein, classes of lytically active peptides such as, for example, "cecropins," "sarcotoxins" and "phage proteins," and specific peptides within such classes, are meant to include the lytically active analogues, homologues, mutants or isomers thereof unless otherwise indicated by context. Of these exemplary lytic peptides, those having fewer than about 30 amino acids such as the melittins are generally unsuitable in the present invention because of their lack of specificity as indicated by their hemolytic potential, whereas those with more than about 40 amino acids such as attacins and lysozymes are generally not sufficiently lytic to be of use in the present invention. On the other hand, those having between about 30 and about 40 amino acids, such as cecropins and sarcotoxins are generally more preferred because of their specificity for lysing target cells over non-target cells.

Hydrophilic amino acids generally include and generally have the respective relative degree of hydrophobicity (at pH 7.0; kcal/mol) as follows: aspartic acid (D), −7.4; glutamic acid (E) −9.9; asparagine (N), −0.2; glutamine (Q), −0.3; lysine (K), −4.2; arginine (R), −11.2; serine (S), −0.3; and cysteine (C), −2.8. Hydrophobic amino acids generally include and generally have the respective relative degree of hydrophobicity as follows: histidine (H), 0.5; threonine (T), 0.4; tyrosine (Y), 2.3; tryptophan (W), 3.4; phenylalanine (F), 2.5; leucine (L), 1.8; isoleucine (I), 2.5; methionine (M), 1.3; valine (V), 1.5; and alanine (A), 0.5. Glycine has a relative degree of hydrophobicity of 0 and may be considered to be hydrophilic or hydrophobic.

The amino acid homology of peptides can be readily determined by contrasting the amino acid sequences thereof as is known in the art. Similarly, the amphiphilic homology of peptides can be determined by contrasting the hydrophilicity and hydrophobicity of the amino acid sequences. The amino acid sequences of various preferred lytic peptides are compared in Table 1, with their degree of homology to cecropin B indicated by underscoring homologous amino acids. The hydrophobic and hydrophilic conformational faces of lytic peptides are readily observed by constructing an Edmunson helical wheel which is a superimposed-type end view of the peptide with the side chains of the amino acids of the peptide arranged in their relative axial positions which would be assumed in an α-helical conformation. Helical wheels constructed for the peptides listed in Table I are seen in FIGS. 1–9. These helical wheel constructs illustrate the hydrophilic face h and the hydrophobic face H of each peptide, the numbering of each sequential amino acid appearing in a shaded circle to represent a hydrophobic amino acid or in an unshaded circle to represent a hydrophilic amino acid.

TABLE 1

LYTIC PEPTIDE HOMOLOGY

| Peptide | Amino Acid Sequence[3] | Amino Acid Homology to Cecropin B | Amphiphilic Homology to Cecropin B | Hydrophilic Face Approx. Degrees | Hydrophilic/Total Amino Acids | Hydrophobic Face Approx. Degrees | Hydrophobic/Total Amino Acids |
|---|---|---|---|---|---|---|---|
| Cecropin B[4] | KWK VFK KIE KMG RNI RNG IVK AGP AIA VLG EAK ALG | 100% | 100% | 198 | 11/20 | 162 | 14/16 |
| Cecropin SB-37[4] | KWK VFK KIE KMG RNI RNG IVK AGP AIA VLG EAK ALG MP | 94% | 94% | 198 | 11/20 | 162 | 14/16 |
| Cecropin A[4] | KWK LFK KIE KVG QNI RDG IIK AGP AVA VVG QAT QIA K | 71% | 97% | 198 | 11/20 | 162 | 15/17 |
| Cecropin D[4] | WN PFK ELE KVG QRV RDA VIS AGP AVA TVA NAT ALA K | 50% | 97% | 144 | 9/14 | 216 | 17/21 |
| Shiva 1[4] | RWR LFR RID RVG KQI KQG ILR AGP AIA LVG DAR AVG | 46% | 94% | 198 | 11/20 | 162 | 14/16 |
| Epidopteran[4] | RWK IFK KIE KMG RNI RDG IVK AGP AIE VLG SAK ALG MP | 86% | 97% | 198 | 12/20 | 162 | 14/16 |
| Sarcotoxin 1A | GWL KKI GKK IER VGQ HTR DAT IQG LGI AQQ AAN VAA TAR | ~26% | ~74% | 216 | 15/21 | 144 | 15/18 |
| Sarcotoxin 1B | GWL KKI GKK IER VGQ HTR DAT IQV IGV AQQ AAN VAA TAR | ~23% | ~74% | 216 | 15/21 | 144 | 15/18 |
| Sarcotoxin 1C | GWL RKI GKK IER VGQ HTR DAT IQV LGI AQQ AAN VAA TAR | ~26% | ~74% | 216 | 15/21 | 144 | 15/18 |

Notes:
[1] ☐ = hydrophilic
[2] ■ = hydrophobic
[3] Position 1 is the amine terminus
[4] The carboxy terminus of all peptides herein is amidated except for the sarcotoxins.

Cecropin B is a potent bacteriolytic peptide which occurs naturally and can be obtained from insects as described in the Hultmark et al patents mentioned above, by direct peptide synthesis, or from genetically transformed host cells as described in the aforementioned Publication WO/086/04356. The amino acid sequence of cecropin B is given in Table 1 and the hydrophilicity/hydrophobicity of each amino acid in its sequence is indicated immediately therebelow. The helical wheel construct of cecropin B seen in FIG. 1 illustrates that fourteen of the sixteen amino acids on the hydrophobic face are hydrophobic while eleven of the twenty amino acids on the hydrophilic face are hydrophilic, for a total of eleven "imperfections". It is contemplated that the removal or replacement of $Gly^{23}$ and $Pro^{24}$ would result in a more lytic peptide with only six imperfections in the amphiphilic helical conformation. In addition, proline is known to disrupt the helical conformation, and its removal may permit a more helical conformation and, hence, more lytic activity. Note that the helical wheel constructs for cecropin SB-37, cecropin D and Shiva 1 have been constructed assuming that the end region prolines would disrupt the α-helical conformation there and this is indicated by placing proline and the preceding amino acids outside the "wheel."

Cecropin SB-37 is an analogue which was prepared using a peptide synthesizer and is about as lytically active as cecropin B. It has 94% homology therewith in its amino acid sequence and its amphiphilicity. As seen in the helical wheel construction of FIG. 2, two of the seventeen amino acids are hydrophilic on the hydrophobic face, while eight of twenty are hydrophobic on the hydrophilic face. It is similarly contemplated that if $Gly^{23}$ and $Pro^{24}$ were removed or replaced, it would have only five imperfections in the amphiphilic conformation, and thus be more lytically active.

Similarly, the other naturally occurring lytic peptides cecropin A, cecropin D, lepidopteran, sarcotoxin 1A, sarcotoxin 1B and sarcotoxin 1C fit the amphiphilic helical conformation of cecropin B as indicated in Table 1 and FIGS. 3, 4 and 6–9. With the exception of cecropin A which is about as lytically active as cecropin B and SB-37, these peptides are generally less lytically active against eucaryotes than cecropin B. However, it is likewise contemplated that the lytic activity thereof may be improved by removing amino acids from the sequence thereof, for example, $Val^{19}$ and $Ile^{20}$ from cecropin D or $Gly^{23}$ and $Pro^{24}$ from lepidopteran or cecropin A.

Figure 5:
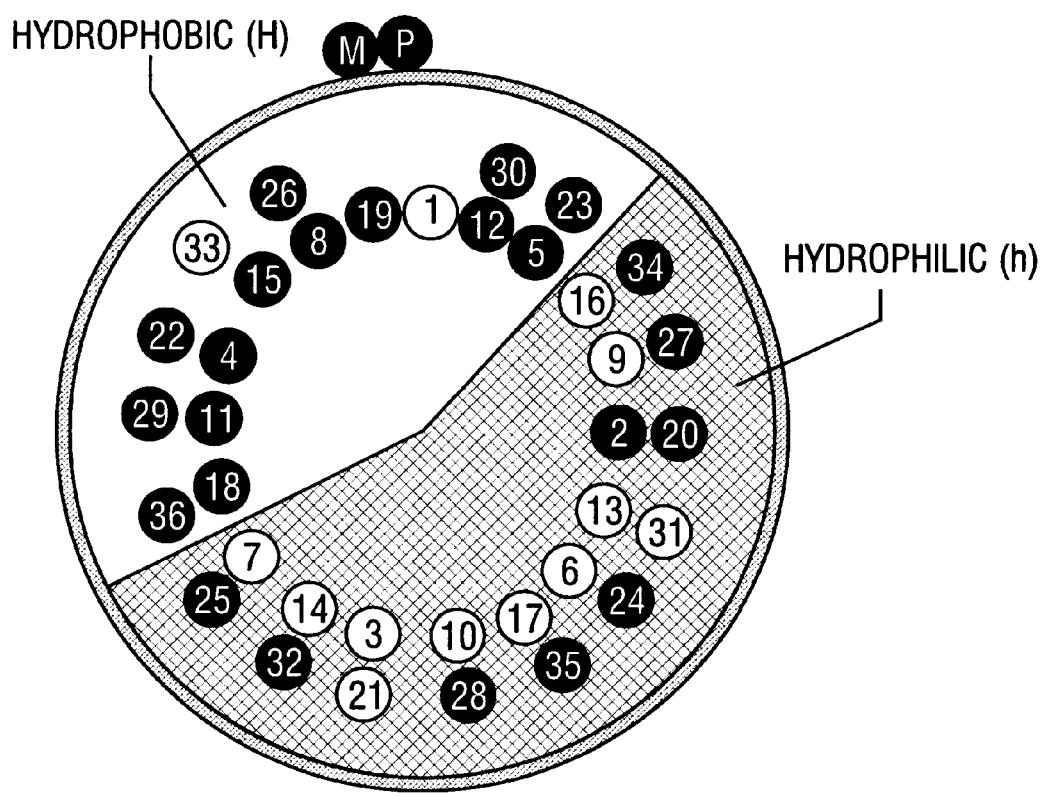
FIG. 5 is an Edmundson helical wheel construct for Shiva 1.
Figure 6:
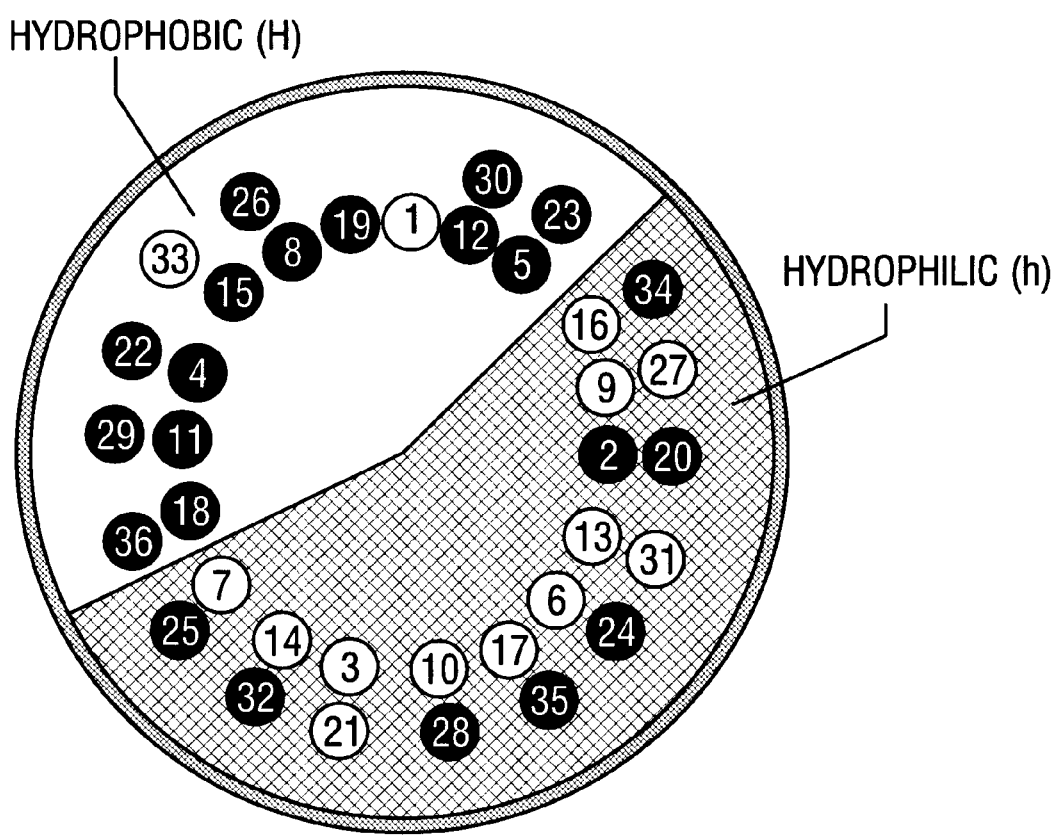
FIG. 6 is an Edmundson helical wheel construct for lepidopteran.
Figure 7:
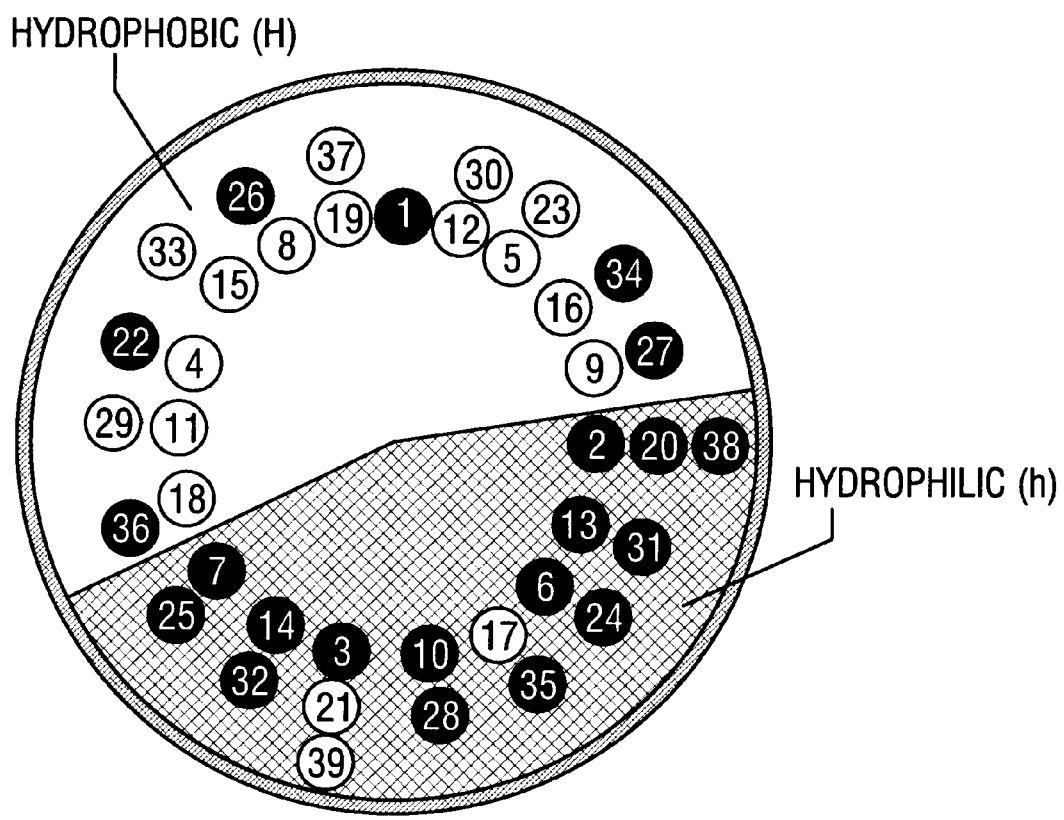
FIG. 7 is an Edmundson helical wheel construct for sarcotoxin 1A.
Figure 8:
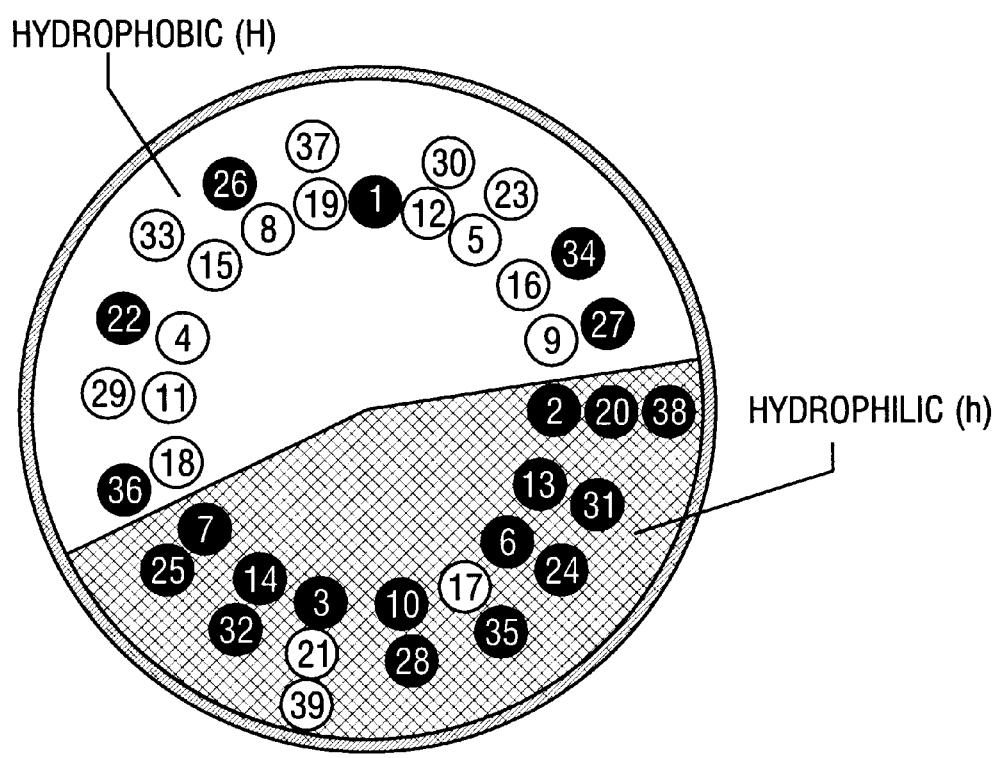
FIG. 8 is an Edmundson helical wheel construct for sarcotoxin 1B.
Figure 9:
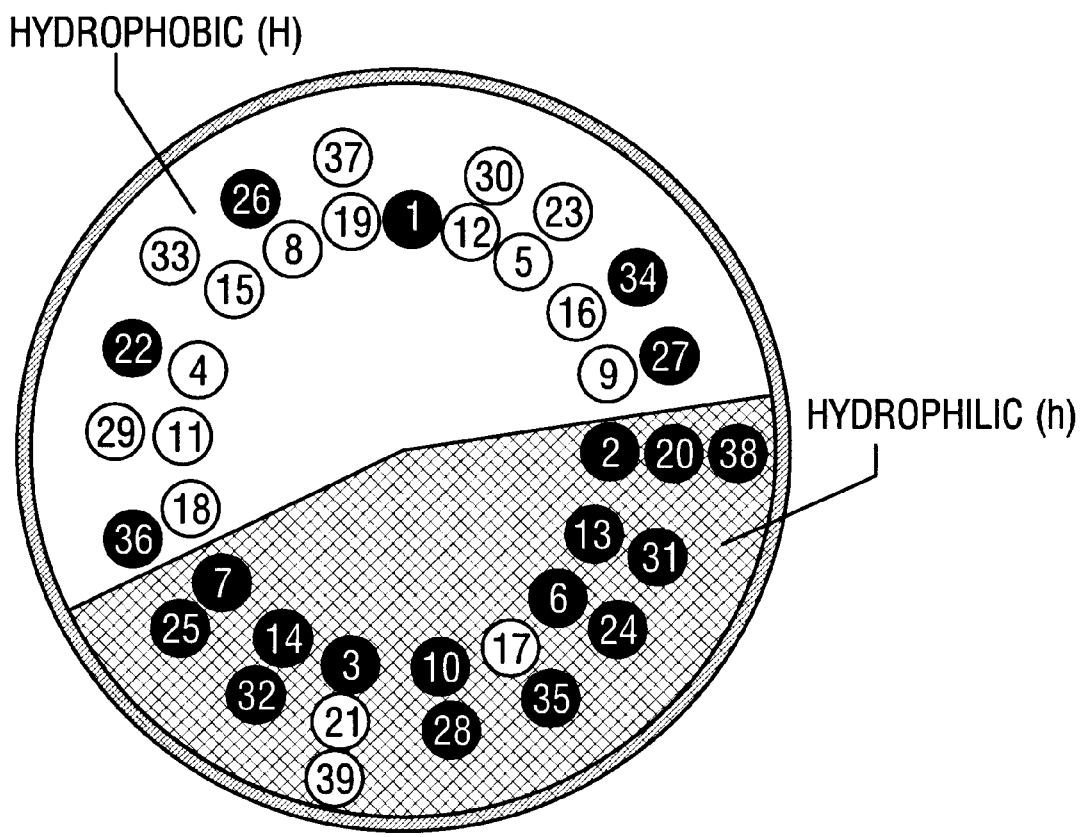
FIG. 9 is an Edmundson helical wheel construct for sarcotoxin 1C.

Another peptide designated herein as "Shiva 1" was prepared using a peptide synthesizer and has the amino acid sequence indicated in Table 1 and the corresponding helical wheel construction seen in FIG. 5. While this peptide has only a 46% amino acid homology with cecropin B, its amphiphilic homology therewith is 100%. Quite surprisingly, however, Shiva 1 is generally much more lytically active than cecropin B, and it is contemplated that its lytic activity may be further enhanced by removal or replacement of $Gly^{23}$ and $Pro^{24}$.

A cecropin SB-37 homologue designated herein as "*cecropin SB-37" is identical thereto except for the substitution of glutamic acid in the fourth position (for tryptophan; corresponding to the second position of cecropin B) and luecine in the eighth position (for lysine; corresponding to the sixth position in cecropin B). Substitutions in these positions may reduce the lytic activity of the cecropin SB-37 against procaryotes by as much as 90% as reported in Andreu et al (1985) mentioned above. Quite surprisingly, however, it has been found that the lytic activity of *cecropin SB-37 against eucaryotes such as eucaryotic microorganisms is generally comparable to cecropin SB-37.

The lytic peptides may be used alone, or in combination with other lytic peptides. It has been found that the lytic activity of the peptides used in the present method may be used to synergistically enhance the lytic activity of a less lytic peptide which may not otherwise be sufficiently lytic to be used in the present methods. For example, the lytic activity of cecropin or sarcotoxin is synergistically enhanced when used in combination with lysozyme. In general, the lytic activity of a mixture of 10 moles lysozyme and 0.1–100 moles cecropin, preferably 1–10 moles cecropin, is more lytically active than a molar equivalent of either cecropin or lysozyme alone. Such synergistic blends may be used not only to lyse or inhibit eucaryotes, but also bacteria. It is contemplated that such a mixture can be advantageously used in pharmaceutical preparations containing a pharmaceutical carrier for administration to man or other higher animals, in foodstuffs and other products as an antibacterial preservative, and in agricultural applications, for example, in a spray applied in an effective amount to crops to prevent infection by, or to inhibit plant pathogens.

The present method is effective to lyse various types of eucaryotic cells such as eucaryotic microorganisms, mammalian neoplastic cells and cells infected with intracellular pathogenic microorganisms. Eucaryotic microorganisms include, for example, fungi such as yeasts, and protozoans such as sarcodina, mastigophora, ciliata and sporozoa. The lytic peptides are particularly effective against *Trypanosoma cruzi* and *Plasmodium falciparum* which are the causitive agents of Chagas disease and malaria, respectively, and are also contemplated as being particularly effective against *Trypanosoma gambiense* which is the causative agent of African sleeping sickness. The method of the present invention is useful to lyse or inhibit cancer cells such as lymphomas, leukemias and carcinomnas, and particularly mammalian cancer cells of these types.

Suitable infected eucaryotes subject to lysis or inhibition according to the present method include cells infected with intracellular pathogenic microorganisms such as viruses, bacteria, fungi, or protozoans. Specific representative examples of such pathogens, the host cells of which are contemplated as suitable for lysis or inhibition according to the present method, include protozoa such as *P. falciparum, T. cruzi,* bacteria such as *Listeria monocytogenes, Brucella abortus* and viruses such as parainfluenza, measles and herpes simplex II. The method is particularly effective for the treatment of DNA virus-infected cells, such as herpes simplex II. Such pathogens grow or replicate within the infected cell and are generally protected from inhibition or lysis by the membrane of the host cell. However, the method of the present invention results in lysis of the host cell so that the intracellular pathogen is subsequently destroyed or subject to lysis or inhibition with the lytic peptides of the present invention or another inhibiting agent since it is no longer protected by the host cell membrane.

In accordance with the present method, the lytic peptide is used to lyse or otherwise inhibit eucaryotic cells by contacting the cells with the peptide. The amount of the lytic peptide necessary to induce cell lysis will usually be sufficient to provide a peptide concentration in the medium containing the cells of at least 1 µM, but it is contemplated that less than this amount may be sufficient in some circumstances. On the other hand, lytic peptide concentrations above about 200 µM will usually not significantly improve cell lysis, although concentrations higher than 200 µM can be used. Preferably, the lytic peptide concentration is in the range of 20–200 µM, and especially 50–100 µM.

In a system in which the cells contacted with the lytic peptide are cultured or grown for obtaining biological or biochemical products therefrom, a cytoplasmic product may be desirably recovered from the lysed cells. For example, the recovery of a product such as interferon may be facilitated by treating cells producing the product with a lytic peptide in combination with cytoskeletal formation inhibitor such as cytochalasin B, avoiding the use of detergents which complicates purification of the desired product.

In a preferred embodiment, the target cells to be lysed are lysed or otherwise inhibited in the presence of non-target cells. For example, the target cells may be an in vitro culture, mixture, or suspension, or may be target cells in a higher animal host, particularly chordate animals and chordate or nonchordate aquacultural animals, and especially mammals such as man. In such a situation, some degree of care is exercised in the selection of the lytic peptide and its concentration to avoid substantial lysis or inhibition of the non-target cells. For use in vivo, an amount of lytic peptide in the range of from about one mg/kg to about 100 mg/kg is usually sufficient to effect the desired inhibition and avoid substantial inhibition of the non-target or host cells, although this dosage may be increased or decreased, or repeated in a series of applications. The peptide may be introduced directly into the higher animal in any conventional manner, e.g. by injection of the peptide in a pharmaceutically acceptable carrier intramuscularly, subcutaneously, intravenously, or intraperitoneally, and preferably at or near the site of infection or cancer. Where there may be a relatively high incidence of target cells in the host, particularly in advanced stages of infection or cancer, additional caution should be exercised since rapid lysis of such a large number of target cells may induce a host reaction to the products of the lytic or inhibitory activity.

Although the present invention is not bound or limited by theory, it is believed that the membranes of the lower eucaryotes are generally subject to lysis by lytic peptides because of the differences in their membranes and cytoskeletal components. However, the membranes of normal cells of the higher eucaryotes somehow prevent lysis, possibly for example, by the ability of their well-developed cytoskeletons to quickly repair any membrane damage caused by the lytic peptide. On the other hand, higher eucaryotic cells with an aberrant cytoskeleton, such as neoplastic or infected cells, are generally unable to prevent lysis by the lytic peptide in the present method.

Quite unexpectedly, it has also been found that the lytic peptide can also stimulate the proliferation of fibroblasts and mitogen activated lymphocytes by contacting the lymphocytes or fibroblasts with an effective amount of a stimulating peptide. As used herein, the term "stimulating peptide" includes not only the preferred lytic peptides described hereinabove having from about 30 to about 40 amino acids, but also includes such peptides having fewer than 30 or more than 40 amino acids containing an active form of the portion of such lytic peptides inducing such stimulation, whether or not they are lytically active. Specifically contemplated stimulating peptides include peptides having the first approximately 15–20 amino acids from the amine terminus of lytic peptides such as cecropins and sarcotoxins. In this sense, "stimulation" means an enhancement of proliferation in any system in which it can be observed or measured, and the stimulating property of such peptides may or may not be related to their lytic property. Preferred stimulating peptides are cecropin A, cecropin SB-37, *cecropin SB-37, cecropin B, cecropin D and Shiva 1, and particularly cecropin SB-37 for stimulating fibroblasts and Shiva 1 for stimulating lymphocytes. For convenience, reference is made hereinbelow to cecropin by way of example with the understanding that other stimulating peptides may be used.

Generally, lymphocytes must be activated by a mitogen, or an antigen reactive with antibodies expressed by the lymphocytes, before any stimulation thereof by a stimulating peptide such as cecropin. Mitogens include, for example, phytohemagglutinin, pokeweed mitogen, concanavilin A, substances for which lymphocytes have developed "memory" such as tetanus toxoid, and the like. Thus, in one embodiment, activated lymphocytes (e.g., lymphocytes in the presence of a mitogen) or fibroblasts are contacted with a stimulating peptide in vitro to increase proliferation thereof. In this manner, the production of biological products by lymphocytes, for example, such as interferon and interleukin-2, may be enhanced by culturing the lymphocytes in the presence of, for example, pokeweek mitogen and cecropin.

In accordance with this embodiment, the lymphocytes or fibroblasts to be stimulated are contacted with an effective amount of cecropin, generally an amount sufficient to provide a concentration in the medium containing the lymphocytes or fibroblasts of from about 1 to about 50 $\mu$M. In a preferred embodiment in which the stimulating peptides are administered in vivo, contemplated dosages of cecropin range from about one to about ten mg/kg. The cecropin may be introduced into the animal to be treated by injection in a suitable pharmaceutical carrier such as saline solution, for example, intramuscularly, subcutaneously, intravenously or intraperitoneally, preferably at or near the site where such stimulation is desired, e.g. a wound, graft, injury or infection. The treatment may be repeated as necessary to sustain the proliferative stimulation of the lymphocytes or fibroblasts.

Although the present invention is not bound or limited by any theory, it is believed that the stimulation of fibroblasts and lymphocytes results from the binding of the amphiphilic, $\alpha$-helical amine terminus portion or end of the preferred lytic peptide to lymphocyte and fibroblast cell membranes. No binding activity is believed to be associated with the generally hydrophobic tail or carboxy terminus end or portion of cecropin or sarcotoxin. Thus, where lytic activity is not beneficial or desired, lymphocytes and/or fibroblasts can be stimulated by a shorter peptide from which the hydrophobic tail has been removed, i.e. the remaining head including the first 15–25, and preferably the first 18–20 amino acids in the cecropin or sarcotoxin sequence.

In another embodiment of the invention, a lytic and/or stimulating peptide is introduced into a higher animal by placing cells into the animal which have an expressible gene coding for the peptide. Such cells may be prepared by genetically transforming cells such as bone marrow cells, embryos, hematapoietic stem cells, and the like. Techniques for such transformation are well known in the art and include, for example, transfection with retroviral vectors, electroporation, microinjection and the like.

The invention is illustrated by way of the following examples.

EXAMPLE 1

In Vitro Effect of Cecropin SB-37 on *T. cruzi* Trypomastigotes

*Trypanosoma cruzi* trypomastigotes were suspended at $10^5$ cells/ml in minimum essential medium ("MEM") and 10% heat-inactivated fetal bovine serum ("MEM-FBS") containing 100 $\mu$M cecropin SB-37. Control trypomastigotes were suspended in the same medium without the cecropin SB-37. After one hour in suspension, the treated trypomastigotes exhibited a 90% reduction in viability, as assessed by microscopically counting viable cells, compared to untreated trypomastigotes under otherwise identical conditions. The reduction in viability was verified by adding the treated and untreated trypomastigotes suspensions to Vero cells in MEM-BFS at $10^5$ cells/ml in a 1:1 ratio of trypomastigotes (as counted prior to cecropin treatment) to Vero cells and culturing 24 hours in microscope slide chambers at 37° C. in a 5% $CO_2$ atmosphere. Based on counts of infected Vero cells, the treated trypomastigotes showed a significantly decreased level of parasitemia compared to the Vero cells with the untreated trypomastigotes.

EXAMPLE 2

In Vitro Effect of Cecropin SB-37 on *T. cruzi* Intracellular Amastigotes in Vero Cells Vero cells at $10^5$ cells/ml in MEM-FBS were mixed with *Trypanosoma cruzi* in the trypomastigote stage at $10^5$ cells/ml in the same medium at a 1:1 ratio of Vero cells to trypomastigotes. The mixture of Vero cells and trypomastigotes was cultured at 37° C. in a 5% $CO_2$ atmosphere in microscope slide chambers. At 24 hours, cecropin SB-37 was added to the chambers, except for a set of controls, at a final concentration of 100 μM. The number of intracellular amastigotes per hundred Vero cells was determined every 24 hours by fixation with formalin, staining with geimsa and counting several hundred Vero cells taken along a line down the microscope slide. The results are presented in Table 2.

TABLE 2

In Vitro Effect of Cecropin SB-37 On *T. cruzi* Intracellular Amastigotes in Vero Cells

| Hours Post *T. cruzi* Addition | Amastigotes/ 100 Vero Cells Control | Amastigotes/ 100 Vero Cells Treated | Cells Infected % Control | Cells Infected % Treated |
|---|---|---|---|---|
| 48 | 20 | 15 | 15 | 14 |
| 72 | 50 | 5 | 16 | 2.5 |
| 96 | 225 | 0 | 14 | 0 |

The foregoing technique was used to determine the $LD_{50}$ of Shiva 1 and cecropin SB-37 (the concentration of each peptide required to obtain a 50% reduction in the number of Vero cells infected with trypoastigotes over a one hour period relative to the number of infected Vero cells incubated in the absence of the peptide for the same period). The $LD_{50}$ for cecropin SB-37 was about 90 μM, while that for Shiva 1 was about 9 μM, indicating that Shiva 1 is about ten times as effective as cecropin SB-37 against *T. cruzi* infection.

EXAMPLE 3

In Vitro Effect of Cecropin B and Cecropin SB-37 on *P. falciparum* In Human Red Blood Cells

*Plasmodium falciparum* was added at 0.0625, 0.125, 0.25 and 0.5 percent parasitized red blood cells (PPRC) to flasks containing 50 ml human red blood cells in RPMI and 10 μM hypoxanthine containing 50 μCi $^3$H-hypoxanthine at 150 ml final volume. The mixture was incubated one week at 37° C. in a 5% $CO_2$ atmosphere. Cecropin B and cecropin SB-37 were then added to different flasks at concentrations of 0 (control), 1, 20 and 200 μM. After 24 hours of additional incubation, the red blood cells were harvested by filtration and hypoxanthine uptake was measured by liquid scintillation as an indication of *P. falciparum* viability. The results are seen in Table 3.

TABLE 3

In Vitro Effect of Cecropin B and Cecropin SB-37 on *P. Falciparum* In Human Red Blood Cells

| Cecropin | Concentration μM | $^3$H-Hypoxanthine Uptake (cpm) *P. falciparum (PPC)* 0.0625 | 0.125 | 0.25 | 0.5 |
|---|---|---|---|---|---|
| SB-37 | 0 | 340 | 520 | 1200 | 2720 |
| | 1 | 315 | 470 | 1053 | 2359 |
| | 20 | 295 | 435 | 946 | 1925 |
| | 200 | 20 | 30 | 40 | 60 |
| B | 0 | 395 | 625 | 1333 | 2730 |
| | 1 | 380 | 565 | 1293 | 2860 |
| | 20 | 405 | 495 | 1066 | 2333 |
| | 200 | 25 | 20 | 40 | 50 |

The foregoing procedure was repeated with *P. falciparum* at 0.5 PPRC with the addition of cecropin SB-37 at 0, 25, 50, 75 and 100 μM. The number of infected red blood cells was determined by microscopically counting infected red blood cells after incubation for 24 hours by fixation staining and counting as described in Example 2. The results are presented in Table 4.

TABLE 4

In Vitro Effect of Cecropin SB-37 on *P. Falciparum* In Human Red Blood Cells

| Concentration (μM) | Infected RBC (%) |
|---|---|
| 0 | 8 |
| 25 | 4 |
| 50 | 2.5 |
| 75 | 2 |
| 100 | 1 |

The foregoing procedure and techniques were used to determine the $LD_{50}$ of Shiva 1 and cecropin SB-37 (the concentration of the peptide required to obtain a 50% reduction in $^3$H-hypoxanthine uptake over a 24-hour period relative to untreated infected red blood cells). The $LD_{50}$ for cecropin SB-37 was about 22.5 μM, while that for Shiva 1 was about 10 μM, indicating that Shiva 1 is about twice as effective as cecropin SB-37 against *P. falciparum* infection.

EXAMPLE 4

In Vitro Effect of Cecropin B, Cecropin SB-37 and Melittin on *S. cerevisiae*

The yeast *Saccharomyces cerevisiae* was grown to late log phase by placing a small inoculum in 100 ml nutrient broth containing 10 grams tryptose, 5 grams of yeast extract and 2 grams glucose per liter. The yeast was then pelleted by centrifugation and resuspended at $10^5$ cells/ml in 0.01 M sodium phosphate buffer solution at pH 6.8 (PBS). Cecropin B, cecropin SB-37, melittin and an unrelated control peptide having 15 amino acids were added in varying concentrations to different wells containing $10^5$ cells/well and the wells incubated at 37° C. for 1 hour. Each well was diluted 1000-fold with PBS and plated on glucose agar. The next day the number of surviving cells was determined by taking plate counts. The results are presented in Table 5.

TABLE 5

Effect of Lytic Peptides on *S. cerevisiae*

| Peptide | Plate Count (Thousands) Concentration ($\mu M$) | | | |
|---|---|---|---|---|
| | 0 | 5 | 50 | 750 |
| Control | 500 | 500 | 500 | 500 |
| Melittin | 500 | 260 | 0 | — |
| Cecropin B | 500 | 500 | 75 | 0 |
| Cecropin SB-37 | 500 | 400 | 75 | 0 |

EXAMPLE 5

In Vitro Effect of Cecropin SB-37 and Shiva 1 on Tumor Cells

EL-4 lymphoma cells were suspended in RPMI 1640 at 5,000,000/ml with 500,000 cells per well. Various concentrations of cecropin SB-37 and Shiva 1 were added and the wells incubated at 37° C. in a 5% $CO_2$ atmosphere for one hour. Viability was determined by microscopic observation for trypan blue exclusion. The results are seen in Table 6.

TABLE 6

In Vitro Effect of Cecropin SB-37 and Shiva 1 on EL-4 Cells

| Peptide | Concentration ($\mu M$) | Viability (%) |
|---|---|---|
| Cecropin SB-37 | 0 | 95 |
| | 10 | 90 |
| | 25 | 90 |
| | 50 | 75 |
| | 100 | 20 |
| Shiva 1 | 0 | 95 |
| | 10 | 85 |
| | 25 | 60 |
| | 50 | 50 |
| | 100 | 10 |

The foregoing results illustrate that both peptides are lytically active against EL-4 cells, and that Shiva 1 is about twice as effective as cecropin SB-37. These results were confirmed by chromium release data obtained by incubating $10^6$ EL-4 cells in 0.5 ml of MEM-FBS containing 10% fetal calf serum and 1 $\mu Ci$ of $^{51}Cr$ for 60 minutes at 37° C., centrifuging and washing the incubated EL-4 cells with PBS, and resuspending the EL-4 cells in MEM-FBS. The EL-4 cells were then incubated for 30 minutes in the presence of various peptides at different concentrations. Cytotoxicity was taken as a percentage of chromium released (measured in the culture supernatant) relative to the chromium released by EL-4 cells lysed by detergent. The results are presented in Table 7.

TABLE 7

Effect of Peptides on EL-4 Cells Measured by Chromium Release

| Peptide Concentration ($\mu M$) | Percent Cytotoxicity[1] | | | |
|---|---|---|---|---|
| | Cecropin SB-37 | *Cecropin SB-37 | Shiva 1 | Melittin |
| 100 | 36.42 | 42.47 | 82.35 | 102.43 |
| 50 | 6.63 | 12.19 | 42.73 | 106.81 |

TABLE 7-continued

Effect of Peptides on EL-4 Cells Measured by Chromium Release

| Peptide Concentration ($\mu M$) | Percent Cytotoxicity[1] | | | |
|---|---|---|---|---|
| | Cecropin SB-37 | *Cecropin SB-37 | Shiva 1 | Melittin |
| 25 | 4.49 | 2.45 | 16.7 | 106.65 |
| 10 | 0.0 | 0.0 | 0.37 | 109.65 |

Note for Table 7:
1. Calculated as a percentage of the cpm of culture supernatant divide by the cpm of the supernatant from detergent-lysed cells:

$$\% \text{ cytoxicity} = \frac{\text{cpm (treated cell supernatant)} - \text{cpm (spontaneous release)}}{\text{cpm (detergent lysis)} - \text{cpm (spontaneous release)}}.$$

Similar chromium release data were obtained using the same procedure with a 100 $\mu M$ concentration of peptide, but with EL-4 cell concentrations of $2 \times 10^6$, $10^6$, and $5 \times 10^5$ cells in 0.5 ml medium. The results are presented in Table 8.

TABLE 8

Effect of EL-4 Cell Concentration on Cytotoxicity of Peptides

| Cells per 0.5 ml | Percent Cytotoxicity[1] | | | |
|---|---|---|---|---|
| | Cecropin SB-37 | Shiva 1 | *Cecropin SB-37 | Melittin |
| $2 \times 10^6$ | 93.75 | 84.88 | 89.07 | 105.44 |
| $10^6$ | 89.25 | 89.22 | 80.51 | — |
| $5 \times 10^5$ | 99.64 | 98.74 | 82.48 | — |

Note for Table 8:
1. See Table 7, note 1.

The chromium release data was also obtained by using the supernatant from unlabeled EL-4 cells cultured for 30 minutes in the presence of 100 $\mu M$ peptide as medium for $^{57}Cr$-labeled EL-4 cultured as described above. The percent cytotoxicity calculated as described above was 20.16 for cecropin SB-37, 19.73 for *cecropin SB-37, 41.96 for Shiva 1, and 106.67 for melittin.

EXAMPLE 6

In Vitro Effect of Cecropin SB-37 on Normal and Neoplastic Mammalian Cells

The procedure of Example 5 was repeated with 50 and 200 $\mu M$ cecropin SB-37 using SP2 mouse lymphoma cells, KG-1 human leukemia cells, Daudi human Burkitt's lymphoma cells, non-adherent normal human lymphocytes and adherent 3T3 human fibroblasts. Viability was determined by microscopic observation for trypan blue exclusion. The results are presented in Table 9.

TABLE 9

Effect of Cecropin SB-37 on
Normal and Neoplastic Mammalian Cells

| | Survival (percent) | |
|---|---|---|
| Cell Line | 50 μM SB-37 | 100 μM SB-37 |
| SP2 | 20 | 5 |
| KG-1 | 95 | 0 |
| Daudi | 85 | 0 |
| Non-adherent Normal Human Lymphocytes | 100 | 30 |
| 3T3 | 80 | 80 |

This procedure was repeated with 100 μM cecropin SB-37 using non-adherent normal human lymphocytes, Daudi human Burkitt's lymphoma cells, KG-1 human leukemia cells, U937 human monocytic leukemia cells, and SP2 murine myeloma cells, and determining viability by the trypan blue exclusion method at 15, 30 and 60 minutes following addition of the peptide. The results are presented in Table 10.

TABLE 10

Effect of 100 μM Cecropin SB-37 on
Normal and Neoplastic Mammalian Cells

| | Viability (%) | | |
|---|---|---|---|
| Cell Line | 15 min. | 30 min. | 60 min. |
| Non-adherent normal human lymphocytes | 75 | 80 | 85 |
| Daudi | 70 | 70 | 65 |
| Kgl | 50 | 75 | 50 |
| U937 | 35 | 25 | 15 |
| SP2 | 100 | 40 | 10 |

EXAMPLE 7

In Vitro Effect of Lytic Peptides on Virus-Infected Cells

Simian kidney cells infected with measles virus, parainfluenza virus and herpes simplex II virus were incubated at $10^5$ cells/ml in 1.0 ml total volume of DMEM and 10% FCS in the presence of 100 μM cecropin SB-37, *cecropin SB-37 and Shiva 1 for 1–4 days. Following incubation, the cells were lysed by addition of equal volume of sterile water, and 0.1 ml of supernatant was added to $10^5$ simian kidney cells in 1.0 ml total volume of DMEM/10% FCS and the mixture was cultured for 24 hours. The number of virus-infected cells in the fresh culture was determined by microscopic slide counting. The results are presented in Table 11.

TABLE 11

Titration of Viruses in the
Presence of Lytic Peptides

| | | Number of Infected Cells | | |
|---|---|---|---|---|
| Incubation Period (Days) | Peptide | Measles | Parainfluenza | Herpes Simplex II |
| 1 | Cecropin SB-37 | $10^7$ | $10^4$ | $<10^2$ |
| | *Cecropin SB-37 | $>10^8$ | $>10^8$ | $<10^2$ |
| | Shiva 1 | $>10^8$ | $10^8$ | $10^3$ |

TABLE 11-continued

Titration of Viruses in the
Presence of Lytic Peptides

| | | Number of Infected Cells | | |
|---|---|---|---|---|
| Incubation Period (Days) | Peptide | Measles | Parainfluenza | Herpes Simplex II |
| | Control | $>10^8$ | $>10^8$ | $10^4$ |
| 2 | Cecropin SB-37 | $10^8$ | $10^{7.5}$ | $<10^2$ |
| | *Cecropin SB-37 | $>10^9$ | $>10^9$ | $10^3$ |
| | Shiva 1 | $>10^9$ | $>10^9$ | $10^5$ |
| | Control | $>10^9$ | $>10^9$ | $>10^7$ |
| 3 | Cecropin SB-37 | $10^5$ | $10^{7.5}$ | $<10^2$ |
| | *Cecropin SB-37 | $>10^9$ | $>10^9$ | $<10^2$ |
| | Shiva 1 | $>10^9$ | $10^9$ | $10^5$ |
| | Control | $>10^9$ | $>10^9$ | $10^7$ |
| 4 | Cecropin SB-37 | $10^{7.5}$ | $10^7$ | $<10^2$ |
| | *Cecropin SB-37 | $>10^9$ | $>10^9$ | $>10^7$ |
| | Shiva 1 | $>10^9$ | $>10^9$ | $10^6$ |
| | Control | $>10^9$ | $>10^9$ | $>10^7$ |

These results indicate that lytic peptides are effective in inhibiting virus-infected eucaryotic cells, and particularly effective against DNA viruses such a herpes simplex II. Cecropin SB-37 appears to be more inhibitory than *cecropin SB-37 and Shiva 1.

EXAMPLE 8

In Vitro Proliferation of Lymphocytes With Cecropin SB-37 and Shiva 1

Lymphocytes recovered by density gradient centrifugation were taken from a human subject 5 months after receiving a tetanus vaccination. The lymphocytes were cultured in IMDM containing 10% Hyclone serum at $3 \times 10^6$ cells/ml in the absence (control) or presence of cecropin SB-37 or Shiva 1 at 50 μM, and 5 μg tetanus toxoid. After incubation at 37° C. in a 5% $CO_2$ atmosphere for 96 hours, the relative proliferative response was determined by $^3$H-thymidine uptake. A second control was established with lymphocytes, obtained from a human subject who had not had a recent tetanus vaccination, which were cultured in the absence of peptide and tetanus toxoid. Relative to the second control, the thymidine uptake was 70% and 80% greater for the cells cultured in the presence of cecropin SB-37 and Shiva 1, respectively, but only 60% greater for the first set of controls (cells recently exposed to tetanus toxoid). This demonstrates the ability of the lytic peptides to stimulate lymphocyte proliferation.

The foregoing procedure was repeated with lymphocytes obtained from four different human subjects. The lymphocytes were cultured as described above, but for a period of 72 hours in the presence of cecropin SB-37 at various concentrations and with other known lymphocyte proliferation inducers. The results are presented in Table 13.

TABLE 13

Stimulatory Effect of Cecropin SB-37 on
Human Lymphocyte Cell Proliferation

| | Range of Values(cpm/cpm control) | | | |
|---|---|---|---|---|
| Treatment | 10 μM | 25 μM | 50 μM | 100 μM |
| SB-37 | 0.53–1.32 | 0.44–1.83 | 0.40–1.85 | 0.07–1.43 |
| SB-37 + PHA[1] 1:800 | 0.10–3.67 | 0.24–4.15 | 0.07–2.16 | 0.01–0.09 |

TABLE 13-continued

Stimulatory Effect of Cecropin SB-37 on
Human Lymphocyte Cell Proliferation

| Treatment | Range of Values(cpm/cpm control) | | | |
|---|---|---|---|---|
|  | 10 μM | 25 μM | 50 μM | 100 μM |
| SB-37 + PHA 1:1600 | 0.15–6.82 | 0.11–3.52 | 0.08–2.19 | 0.01–0.09 |
| SB-37 + PWM[2] 1:50 | 0.28–1.95 | 0.25–1.98 | 0.17–1.64 | 0.00–0.71 |
| SB-37 + PWM 1:100 | 0.28–2.37 | 0.29–2.39 | 0.21–2.20 | 0.01–0.81 |
| SB-37 + CONA[3] 50 μg | 0.01–3.23 | 0.01–3.10 | 0.01–2.10 | 0.00–0.80 |
| SB-37 + CONA 25 μg | 0.01–5.75 | 0.01–6.29 | 0.01–4.95 | 0.00–0.45 |

Notes for Table 12:
[1]PHA = phytohemagglutinin.
[2]PWM = pokeweed mitogen.
[3]CONA = concanavalin A.

EXAMPLE 9

In Vitro Stimulation of Fibroblast Proliferation With Cecropin SB-37

3T3 Mouse embryonic fibroblasts were cultured in IMDME without serum at $10^4$ cells per well for 48 hours with cecropin SB-37 and Shiva 1 at various concentrations with or without insulin at 10 μg/ml. Proliferation was assessed by $^3$H-thymidine uptake using a scintillation counter. The results are presented in Table 14.

TABLE 14

Stimulation of Fibroblast Proliferation With Cecropin SB-37

| Peptide Concentration (μM) | $^3$H-Thymidine Uptake ($10^3$ cpm) | | | |
|---|---|---|---|---|
|  | SB-37 | Shiva 1 | SB-37 and Insulin | Shiva 1 and Insulin |
| 10 | 72 | 0 | 60 | 0 |
| 25 | 80 | 0 | 65 | 0 |
| 50 | 120 | 0 | 110 | 0 |
| 100 | 25 | 2 | 30 | 2 |

EXAMPLE 10

In Vivo Screening of Cecropin SB-37 on Mice

Nine BALB/C mice, 4 to 5 weeks of age, maintained on commercial rodent ration fed ad libidum and in general good health were each inoculated with 1.76 mg/day of cecropin SB-37 in PBS intramuscularly for 4 consecutive days. No other change was made in diet or conditions. The mice were observed twice daily and no adverse reactions were noted. At the end of the fourth day, three were sacrificed and examined. After 30 days, three were given an additional 1.76 mg of cecropin SB-37 each. No adverse reactions were noted.

The remaining mice were all sacrificed 7 days after the last inoculation. Examination of organs and tissues indicated no gross pathological changes were present in the organs or at the injection sites. None of these mice produced detectable levels of antibody to the cecropin SB-37.

Following the above procedure, three BALB/C mice were given 110 mg/kg of body weight per day of cecropin SB-37 injected intramuscularly in balanced salt solution for 6 days. White blood cell counts were determined periodically and are reported in Table 14. Ten days after the last inoculation, the mice were again injected intramuscularly with 110 mg/kg of body weight with cecropin SB-37. Observation revealed no adverse effects during the procedure. All three mice were sacrificed 7 days after the final inoculation and tissues were examined. All mice had enlarged spleens but were otherwise unremarkable. No cecropin SB-37 antibodies were detected.

TABLE 14

Effect of Cecropin SB-37 on WBC Count

| Day | WBC Count ($10^3$/ml) | | |
|---|---|---|---|
|  | Mouse 1 | Mouse 2 | Mouse 3 |
| 1 | 13 | 13 | 9 |
| 3 | 14 | 9 | 10 |
| 5 | 15 | 19 | 15 |
| 8 | 21 | 21 | 21 |
| 11 | 23 | 23 | 20 |

EXAMPLE 11

In Vivo Effect of Shiva 1 on Murine Mammary Carcinoma

One BALB/c mouse was given daily injections of 1.76 mg (88 mg/kg) Shiva 1 in PBS for three consecutive days as described in the foregoing examples. The mouse had a large mammary carcinoma into which the Shiva 1 was directly injected. Following the third injection, this mouse died almost immediately. Autopsy revealed shock as the immediate cause of death, and substantial cell death in the carcinoma. It is believed that lower dosages would have avoided shock, but would still have significantly inhibited the carcinoma.

EXAMPLE 12

In Vivo Effect of Cecropin SB-37 on B. Abortus in Mice

A total of 18 BALB/C mice, maintained on commercial rodent ratio fed ad libidum, 4 to 5 weeks of age and in good health were inoculated intraperitoneally with 3 to $5 \times 10^8$ Brucella abortus (an intracellular pathogen) in physiological saline. On the twelfth day post infection, six of the mice were each inoculated intramuscularly with 0.176 mg/day of cecropin SB-37 in PBS, six were treated with 0.176 mg/day of tetracycline and six were given sterile PBS, all for a period of 4 days. Half of the mice in each group were sacrificed on the sixteenth day post infection and spleen tissue examined morphologically, histologically and by culturing according to standard procedures for Brucella abortus. The concentrations found are given in the following Table 15.

TABLE 15

Concentration of Brucella abortus in BALB/c
Mouse Spleen Tissue After
4 Days Treatment (Number per gram of spleen)

| Control | Tetracycline | Cecropin SB-37 |
|---|---|---|
| $8.15 \times 10^3$ | $4.4 \times 10^3$ | $1.59 \times 10^3$ |

The remaining mice were sacrificed on the twenty-third day post infection and examined in the same manner and no difference in result was observed. This result indicates that the lytic peptide cecropin SB-37 is capable of significantly decreasing the level of infection and growth of *Brucella abortus* in mice.

EXAMPLE 13

In Vivo Effect of Cecropin SB-37 on *L. Monocytogenes* in Mice

The procedure of Example 12 was repeated except that another intracellular pathogen, *Listeria monocytogenes,* was used instead of *B. Abortus,* and the control group was untreated (sterile saline injections only). The untreated mice sacrificed five days post infection had an average of 46 million *L. monocytogenes* bacteria in their spleen, in contrast to less than five million in the mice given daily injection of cecropin SB-37.

EXAMPLE 14

Lysozyme/Cecropin Synergism Against *E. Coli*

To a suitable container was added 50 $\mu$l of the bacteria under investigation, in this instance, *E. coli* E/2/64, obtained from Cornell University, and 50 $\mu$l of phosphate buffered saline solution (PBS), prepared from NaCl 80.0 g, KCl 3 g, $Na_2HPO_4$–0.73 g, $KH_2PO_4$–0.2 g, with dilution of 10 ml of mixture with 90 ml of water and sterilization by autoclaving. The *E. coli* were collected in late log phase growth at which the majority of cells were in growth phase at 18–24 hours. In addition, the same mixture was prepared with 5 $\mu$M of cecropin B or cecropin SB-37. The mixtures were incubated at room temperature for 90 minutes. The mixtures were diluted to $10^{-1}$ or $10^{-3}$ with serial dilutions at 7 drops per dilution (10 $\mu$l per drop), and plated on tryptose agar growth media. The plates were incubated for 3 days at room temperature. Plate counts indicated that there was no growth of *E. coli.*

Combinations of both cecropin B and cecropin SB-37 with lysozyme (25:25 $\mu$l mixture) also prevented growth at 0.1 $\mu$M concentrations, but lysozyme itself at concentrations of 10 $\mu$g, 1 mg, and 10 mg per milliliter all showed positive growth of *E. coli* at both $10^{-1}$ and $10^{-3}$ dilutions. Further, lower concentrations of one nanomolar and one micromolar of both cecropin species showed positive *E. coli* growth.

EXAMPLE 15

Lysozyme/Cecropin Syngergism Against *B. Abortus*

The procedure of Example 14 was followed, except the microorganism was *Brucella abortus,* isolated by conventional procedure, the cecropin/bacteria mixture was incubated for one hour at room temperature and then 30 minutes at 37° C., and the plates were incubated at 37° C. The results are shown in Table 16 below.

TABLE 16

Effect of Cecropins on *Brucella abortus*

| Cecropin | Concentration ($\mu$M) | Results |
|---|---|---|
| Cecropin B | 50 | No growth |
| Cecropin SB-37 | 50 | No growth |

Combinations of cecropin SB-37 and cecropin B with lysozyme at 1, 10 and 100 $\mu$g/ml were effective to prevent growth only at the highest concentration of lysozyme with cecropin SB-37; otherwise, some growth of the *Brucella abortus* was noted.

EXAMPLE 16

Lysozyme/Lytic Peptide Synergism Against *P. Aeruginosa*

The procedure of Example 15 was followed with cecropin SB-37 and Shiva 1, alone and in combination with lysozyme at the same molar cencentration of the lytic peptide, against *Pseudomonas aeruginosa.* The results are presented in Table 17.

TABLE 17

*P. aeruginosa* Viability in Lytic Peptide/Lysozyme

| | Viability (%) | | | |
|---|---|---|---|---|
| Peptide Concentration ($\mu$M) | Cecropin SB-37 | Shiva 1 | Lysozyme (1x) | Shiva 1 and Lysozyme(1x) |
| 0 | 100 | 100 | 100 | — |
| 0.01 | 100 | 100 | 100 | 56.6 |
| 0.1 | 79.4 | 69.6 | 82.2 | 25.8 |
| 1.0 | 48.8 | 37.9 | 52.1 | 4.4 |
| 5.0 | 38.5 | 1.5 | 7.9 | 0.2 |
| 7.5 | 0.7 | 0.1 | 0.6 | 0 |
| 25. | 0 | 0 | 0.4 | 0 |

EXAMPLE 17

Lysozyme/Lytic Peptide Synergism Against Staphylococci

The procedure of Example 16 was repeated using *S. intermedius* 19930, *S. intermedius* 20034 and *S. aureus* with lysozyme at ten times the molar concentration of the lytic peptide. The results are presented in Tables 18, 19 and 20, respectively.

TABLE 18

*S. Intermedius* 19930 Viability in Lytic Peptide/Lysozyme

| | Viability (%) | | | |
|---|---|---|---|---|
| Peptide Concentration ($\mu$M) | Cecropin SB-37 | Shiva 1 | Lysozyme (10x) | Shiva 1 and Lysozyme(10x) |
| 0 | 100 | 100 | 100 | — |
| 0.01 | 100 | 100 | 100 | 100 |
| 0.1 | 94.7 | 81.8 | 100 | 79.2 |
| 0. | 69.4 | 65.0 | 81.3 | 65.1 |
| 1.0 | 42.5 | 42.1 | 53 | 43 |
| 5.0 | 36.1 | 35.2 | 49.5 | 17.2 |
| 10. | 5.6 | 1.2 | 34.4 | 1.1 |
| 50. | 0 | 0 | 22 | 0 |

TABLE 19

*S. Intermedius* Viability in Lytic Peptide/Lysozyme

| | Viability (%) | | | |
|---|---|---|---|---|
| Peptide Concentration ($\mu$M) | Cecropin SB-37 | Shiva 1 | Lysozyme (1x) | Shiva 1 and Lysozyme(1x) |
| 0 | 100 | 100 | 100 | 100 |
| 0.01 | 100 | 100 | 100 | 100 |
| 0.25 | 85.4 | 87.1 | 100 | 85.1 |
| 0.5 | 68.0 | 80.0 | 59.0 | 53.4 |
| 0.75 | 62.2 | 60.1 | 42.3 | 41.0 |

TABLE 19-continued

S. Intermedius Viability in Lytic Peptide/Lysozyme

| Peptide Concentration ($\mu$M) | Viability (%) | | | |
|---|---|---|---|---|
| | Cecropin SB-37 | Shiva 1 | Lysozyme (1x) | Shiva 1 and Lysozyme(1x) |
| 5.0 | 35.1 | 4.1 | 38.3 | 4.3 |
| 50. | 0 | 0 | 10.0 | 0 |

TABLE 20

S. aureus Viability in Lytic Peptide/Lysozyme

| Peptide Concentration ($\mu$M) | Viability (%) | | | |
|---|---|---|---|---|
| | Cecropin SB-37 | Shiva 1 | Lysozyme (1x) | Shiva 1 and Lysozyme(1x) |
| 0 | 100 | 100 | 100 | 100 |
| 0 | 100 | 100 | 100 | 100 |
| 0.01 | 100 | 100 | 100 | 100 |
| 0.1 | 100 | 100 | 100 | 100 |
| 0.5 | 81.0 | 50.1 | — | — |
| 1.0 | 47.5 | 24.4 | 51.0 | 31.2 |
| 5.0 | 31.8 | 15.9 | 18.4 | 8.2 |
| 10. | 5.6 | 4.5 | 13.3 | 4.5 |
| 50. | 1.9 | 1.6 | 9.5 | 1.4 |

EXAMPLE 18

Lysozyme Lytic Peptide Synergism Against Plant Pathogens

The procedures of the foregoing examples with the exception of an incubation temperature of 30° C. instead of 37° C., were used to demonstrate the synergistic bactericidal properties of a lytic peptide in combination with lysozyme against common plant pathogens. The results are presented in Table 21.

TABLE 21

Plant Pathogen $LD_{50}$ in Cecropin SB-37/Lysozyme

| Bacteria | $LD_{50}(\mu M)$ | | |
|---|---|---|---|
| | Cecropin SB-37 | Lysozyome | Cecropin SB-37 (+Lysozyme (10x)) |
| Pseudomonas syringae pv. tabaci | 5.20 | >1000 | 0.19 |
| Pseudomonas solanacearum | 64.0 | >1000 | 16.0 |
| Erwinia caratovora suhsp. carotova | 1.48 | >1000 | 0.44 |
| Xanthomonas campestris pv. campestris | 0.57 | >1000 | 0.027 |

Having described the invention above, various modifications of the techniques, procedures, material and equipment will be apparent to those in the art. It is intended that all such variations within the scope and spirit of the appended claims be embraced thereby.

We claim:

1. A method for lysing fungal cells or protozoa cells, comprising:
contacting said cells in vitro or topically with an exogenous lytic peptide in an amount effective to lyse said cells;
wherein said lytic peptide is a cecropin, a sarcotoxin, a lepidopteran, Shiva 1, or a cecropin analog, wherein said cecropin analog has lytic activity.

2. The method of claim 1, wherein said protozoa cells are selected from the group consisting of Trypanosoma and Plasmodium.

3. The method of claim 1, wherein said fungal cells are yeast cells.

4. A method for lysing eucaryotic cells infected with intracellular pathogenic microorganisms, comprising:
contacting said cells in vitro or topically with an amount of an exogenous lytic peptide sufficient to lyse said cells;
wherein said intracellular pathogenic microorganisms are selected from the group consisting of viruses, bacteria, fungi, and protozoa; and
wherein said lytic peptide is a cecropin, a sarcotoxin, a lepidopteran, Shiva 1, or a cecropin analog, wherein said cecropin analog has lytic activity.

5. The method of claim 4, wherein said virus is a DNA virus.

6. The method of claim 4, wherein said virus is parainfluenza, measles, or herpes simplex II.

7. The method of claim 4, wherein said intracellular pathogenic microorganism is a species of Listeria or Brucella.

8. The method of claim 4, wherein said intracellular pathogenic microorganism is a species of Trypanosoma or Plasmodium.

9. The method of claim 1 or 4, wherein said contacting topically is effected on a mammal.

10. The method of claim 1 or 4, wherein said lytic peptide is Cecropin SB-37.

11. The method of claim 1 or 4, additionally comprising contacting said cells with exogenous lysozyme.

12. A method for lysing target eucaryotic lymphoma, leukemia, or carcinoma cancer cells; comprising contacting said target cells in vitro with an effective amount of an exogenous lytic peptide to lyse the target cells; wherein the lytic peptide is a cecropin, a sarcotoxin, a lepidopteran, Shiva 1, or a cecropin analog, wherein said cecropin analog has lytic activity.

13. A method as recited in claim 12, wherein said target cells are mammalian lymphoma, mammalian leukemia, or mammalian carcinoma cancer cells.

14. A method as recited in claim 13, wherein said lytic peptide is Cecropin SB-37.

15. A method for treating a mammalian host diagnosed as infected with a pathogenic virus, bacteria, fungi, or protozoa; comprising topically or orally administering an exogenous lytic peptide; wherein said lytic peptide is a cecropin or a sarcotoxin.

16. The method of claim 15, wherein said lytic peptide is cecropin SB-37.

17. The method of claim 15, wherein said virus is a DNA virus.

18. The method of claim 15, wherein said virus is parainfluenza, measles, or herpes simplex II virus.

19. The method of claim 15, wherein said bacteria is a species of Listeria or Brucella.

20. The method of claim 15, wherein said protozoa is a species of Trypanosoma or Plasmodium.

21. A method for treating a mammalian host diagnosed with cancer, comprising topically or orally administering an exogenous lytic peptide; wherein said lytic peptide is a cecropin or a sarcotoxin.

22. The method of claim 21, wherein said lytic peptide is cecropin SB-37.

23. A method for treating a mammalian host diagnosed as infected with a virus, bacteria, fungi, or protozoa; comprising administering in vivo an exogenous lytic peptide; wherein said lytic peptide is a cecropin or a sarcotoxin.

24. The method of claim 23, wherein said virus is a DNA virus.

25. The method of claim 23, wherein said virus is parainfluenza, measles, or herpes simplex II virus.

26. The method of claim 23, wherein said bacteria is a species of Listeria or Brucella.

27. The method of claim 23, wherein said protozoa is a species of Trypanosoma or Plasmodium.

28. The method of claim 23, wherein said lytic peptide is cecropin SB-37.

29. The method of claim 23, wherein said in vivo administration comprises intramuscular, subcutaneous, intravenous, or intraperitoneal administration.

30. A method for treating a mammalian host diagnosed with cancer, comprising administering in vivo an exogenous lytic peptide; wherein said lytic peptide is a cecropin or a sarcotoxin.

31. The method of claim 30, wherein said lytic peptide is cecropin SB-37.

32. The method of claim 30, wherein said in vivo administration comprises intramuscular, subcutaneous, intravenous, or intraperitoneal administration.

* * * * *